US012618174B2

(12) United States Patent
Medek et al.

(10) Patent No.: US 12,618,174 B2
(45) Date of Patent: May 5, 2026

(54) METHOD OF PRODUCTION OF FIBERS AND A DEVICE FOR CARRYING OUT THE METHOD

(71) Applicant: CONTIPRO A.S., Dolni Dobrouc (CZ)

(72) Inventors: Tomas Medek, Usti nad Orlici (CZ); Eliska Sestakova, Keblice (CZ); Marek Pokorny, Cenkovice (CZ); Vladimir Velebny, Zamberk (CZ)

(73) Assignee: CONTIPRO A.S., Dolni Dobrouc (CZ)

( * ) Notice: Subject to any disclaimer, the term of this patent is extended or adjusted under 35 U.S.C. 154(b) by 162 days.

(21) Appl. No.: 18/699,118

(22) PCT Filed: Oct. 5, 2022

(86) PCT No.: PCT/CZ2022/050101
§ 371 (c)(1),
(2) Date: Apr. 5, 2024

(87) PCT Pub. No.: WO2023/056996
PCT Pub. Date: Apr. 13, 2023

(65) Prior Publication Data
US 2025/0230582 A1 Jul. 17, 2025

(30) Foreign Application Priority Data
Oct. 7, 2021 (CZ) ................................ CZ2021-469

(51) Int. Cl.
*D01F 9/00* (2006.01)
*A61L 31/10* (2006.01)
(Continued)

(52) U.S. Cl.
CPC ................ *D01F 9/00* (2013.01); *A61L 31/10* (2013.01); *D01D 1/103* (2013.01); *D01D 7/00* (2013.01);
(Continued)

(58) Field of Classification Search
CPC .................................................... D04H 1/4326
See application file for complete search history.

(56) References Cited

U.S. PATENT DOCUMENTS

| | | |
|---|---|---|
| 5,622,707 A | 4/1997 | Dorigatti et al. |
| 8,641,960 B1 | 2/2014 | Medeiros et al. |

(Continued)

FOREIGN PATENT DOCUMENTS

| | | |
|---|---|---|
| CN | 110424059 A | 11/2019 |
| CZ | 303879 B6 | 6/2013 |

(Continued)

OTHER PUBLICATIONS

Jyotsnendu, Giri. (Nov. 23, 2018). A Device For Fabricating Micro and Nano Fibers and Particles. pp. 1-47. Retrieved from https://raiithold.iith.ac.in/4543/ on Jan. 17, 2023.

*Primary Examiner* — Emmanuel S Luk
(74) *Attorney, Agent, or Firm* — Ingrassia Fisher & Lorenz, LLP | IF&L

(57) ABSTRACT

The present invention refers to a method and device for the preparation of microfibres and nanofibres based on hyaluronic acid and/or a water-soluble metal or non-metal salt thereof or a mixture of salts and/or a derivative of hyaluronic acid by method of dry spinning, and two-dimensional or three-dimensional fibrous materials from this microfibres and nanofibres. The resulting 2D or 3D materials can be for example in the shape of layer or cotton wool. Furthermore, the present invention refers to a device for performing this method, that contains an extrusion part containing a pass-through channel, that has an inlet opening for feeding the spinning solution and a dispensing opening for dispensing the spinning solution and furthermore the device contains an air nozzle, the air outlet opening of which is arranged to direct the exiting air into the area surrounding
(Continued)

the dispensing opening of the extrusion part parallel to the axis of the dispensing opening of the extrusion part.

13 Claims, 14 Drawing Sheets

(51) Int. Cl.

| | |
|---|---|
| ***D01D 1/10*** | (2006.01) |
| ***D01D 7/00*** | (2006.01) |
| ***D01D 10/06*** | (2006.01) |
| ***D01F 1/06*** | (2006.01) |
| ***D01F 1/10*** | (2006.01) |
| ***D04H 1/4326*** | (2012.01) |

(52) U.S. Cl.

CPC ............... *D01D 10/06* (2013.01); *D01F 1/06* (2013.01); *D01F 1/103* (2013.01); *D04H 1/4326* (2013.01)

(56) References Cited

U.S. PATENT DOCUMENTS

| | | | |
|---|---|---|---|
| 8,753,671 B2 | 6/2014 | Domard et al. | |
| 9,545,364 B2 | 1/2017 | Glenn, Jr. et al. | |
| 2009/0220579 A1* | 9/2009 | Hassingboe ............. | D01D 5/14 428/375 |
| 2010/0096769 A1 | 4/2010 | Ichiro et al. | |
| 2013/0309494 A1* | 11/2013 | Burgert ............... | C08B 37/0072 428/401 |
| 2013/0312638 A1 | 11/2013 | Parker et al. | |
| 2014/0030315 A1* | 1/2014 | Johnson .................. | A61L 27/60 424/444 |
| 2015/0272855 A1* | 10/2015 | Kim ......................... | A61K 8/65 424/401 |
| 2021/0228684 A1* | 7/2021 | Delisle .................... | A61P 27/02 |
| 2022/0025334 A1 | 1/2022 | Elfenbein | |

FOREIGN PATENT DOCUMENTS

| | | |
|---|---|---|
| CZ | 304651 B6 | 8/2014 |
| CZ | 304977 B6 | 2/2015 |
| CZ | 2013913 A3 | 6/2015 |
| CZ | 308010 B6 | 10/2019 |
| EP | 3346032 A1 | 7/2018 |
| JP | 2007262595 A | 10/2007 |
| WO | 8910941 A1 | 11/1989 |
| WO | 9417837 A1 | 8/1994 |
| WO | 2005028632 A2 | 3/2005 |
| WO | 2012089179 A1 | 7/2012 |
| WO | 2014082611 A1 | 6/2014 |
| WO | 2014127099 A2 | 8/2014 |
| WO | 2017039335 A1 | 3/2017 |
| WO | 2018235745 A1 | 12/2018 |
| WO | 2020124072 A1 | 6/2020 |

* cited by examiner

METHOD OF PRODUCTION OF FIBERS AND A DEVICE FOR CARRYING OUT THE METHOD

TECHNICAL FIELD

The invention relates to a method and device for preparation of microfibres or nanofibres based on hyaluronic acid and/or its water-soluble metal or non-metal salt or a mixture of salts and/or its derivative by the method of dry spinning, and two-dimensional or three-dimensional fibrous materials made of these microfibres or nanofibres. Furthermore, the invention relates to a device for performing this method.

STATE OF THE ART

Hyaluronic acid (HA or hyaluronan) is a linear polysaccharide formed by repeating disaccharide units composed of D-glucuronic acid and N-acetylglucosamine according to the formula I (I)

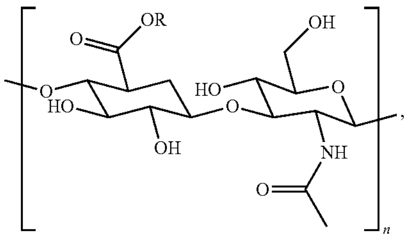

where R is $H^+$ or a metal cation.

Hyaluronan is found in the intercellular spaces of most human tissues, where it influences a number of processes including the maintenance of homeostasis, regeneration and wound healing. Hyaluronan products have a variety of forms, such as injectable solutions and gels, foils or textiles. These products are used in medicine and cosmetics, for example, as medical devices for wound healing, treatment of osteoarthritis, prevention of postoperative adhesions or reduction of wrinkles.

In order to modify the properties of the native hyaluronan, a number of hyaluronan derivatives have been prepared in the past.

Hyaluronan chloramide is a derivative of hyaluronic acid in which most of the hydrogens of the amide group —NH—CO— are substituted by a chlorine atom to —NCl—CO—. The preparation thereof and the properties thereof, which include antimicrobial, antifungal and antiviral activity, are described in the document CZ 308010.

Crosslinkable hyaluronan derivatives are derivatives containing groups enabling the connection of polymer chains by covalent bonds. These include 3-(2-furanyl)acryloyl ester of hyaluronan and tyramine hyaluronan.

Hyaluronan 3-(2-furanyl)acryloyl ester can be crosslinked by UV radiation in the solid phase. The synthesis and electrospinning thereof are described in the document CZ 304977 B6.

Tyramine hyaluronan is the name for various conjugates of hyaluronan with tyramine, which can be used, for example, to prepare crosslinked hydrogels. The synthesis of tyramine hyaluronan according to Formula II is described in the document CZ 303879 B6. Crosslinking of tyramine hyaluronan using riboflavin and UV radiation is described in the publication Donnelly, P. E., Chen, T., Finch, A., Brial, C., Maher, S. A., & Torzilli, P. A. (2017). Photocrosslinked tyramine-substituted hyaluronate hydrogels with tunable mechanical properties improve immediate tissue-hydrogel interfacial strength in articular cartilage. Journal of Biomaterials Science, Polymer Edition, 28(6), 582-600.

(II)

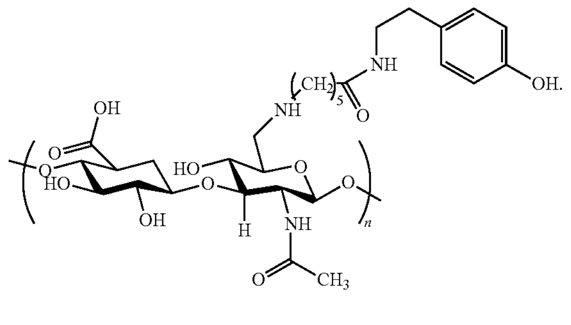

Non-polar derivatives of hyaluronan contain hydrophobic substituents. They can be classified to esters and acylated derivatives. The esters are hyaluronan benzyl ester and hyaluronan ethyl ester, their preparation is described in document U.S. Pat. No. 5,622,707.

The acylated derivatives are hyaluronan derivatives in which primarily the primary alcohol of N-acetyl-glucosamine and to a lesser extent the secondary alcohols of glucuronic acid are acylated with fatty acids. The acyl group can be, for example, caproyl (hexanoyl), capryloyl (octanoyl), caprinoyl (decanoyl), lauroyl (dodecanoyl), myristoyl (tetradecanoyl), palmitoyl (hexadecanoyl), stearoyl (octadecanoyl) and oleoyl (octadec-9-enoyl). Examples of the preparation of acylated derivatives are given in document WO 2014082611 A1.

In the field of spinning of hyaluronan and derivatives thereof, two types of technologies clearly prevail: electrospinning and wet spinning.

In electrospinning, the polymer solution is drawn into a fibre shape by the action of electrical forces. The preparation of fibres from an aqueous solution of hyaluronan by electrospinning is very difficult, therefore fibres are usually prepared from a mixture of hyaluronan with other polymers, for example polyethylene glycol or gelatin. Alternatively, pure hyaluronan can be spun by classical electrospinning when dissolved in a mixture of water and dimethylformamide or by the electroblowing method when dissolved in an aqueous solution of HCl at pH=1.5, which method uses, in addition to the electric field, an air stream that draws and dries the fibre (Lee, K. Y., Jeong, L., Kang, Y. O., Lee, S. J., & Park, W. H. (2009). Electrospinning of polysaccharides for regenerative medicine. Advanced Drug Delivery Reviews, 61(12), 1020-1032).

Hyaluronan fibres prepared by electrospinning are mostly deposited on a collector in the form of a thin non-woven fabric (two-dimensional structure). Document WO 2020/124072 A1 discloses a method of expanding two-dimensional nanofibrous layers into a three-dimensional structure by exposure to gas bubbles. Document CZ 2013-913 A3 describes the spinning conditions under which a bulky layer of nanofibres is directly formed.

One of the drawbacks of the hyaluronan electrospinning technology is its limitation to the preparation of fibres of small diameters, in most cases less than 1 micrometer. Such fibres are characterized by low stiffness, low strength and a very fast dissolution in an aqueous environment. Furthermore, the solvents used for spinning pure hyaluronan are either unsuitable for use in healthcare due to their toxicity (e.g., dimethylformamide), or cause hyaluronan degradation (e.g., acid hydrolysis in an aqueous HCl solution). In case of using a mixture of hyaluronan with another polymer, the overall properties of the material change.

The principle of wet spinning of a polymer is the extrusion of a polymer solution into a coagulation bath, in which the coagulation (precipitation) of the polymer into a fibre form occurs and the original solvent diffuses bidirectionally from the fibre into the coagulation bath and from the coagulation bath into the fibre. For example, the document U.S. Pat. No. 8,753,671 B2 discloses the preparation of an endless fibre (filament) from hyaluronan by wet spinning. The document WO 94/17837 discloses the preparation of non-woven fabrics from staple fibres obtained by cutting the hyaluronan ester filament prepared by wet spinning, the cohesion of these fibres is additionally improved by chemical bonding. The document CZ 304651 B6 describes the direct preparation of staple fibres by hyaluronan spinning in a non-stationary coagulation bath and their subsequent processing into a non-woven fabric with steps including at least filtration and drying of the fibres.

The main disadvantage of the wet spinning technology is the two-way mass transfer during the fibre precipitation, which makes the fibre formation process slower than in other types of spinning. After removing the fibres from the coagulation bath, it is necessary to dry them from the residues of the coagulation bath, often the residues of the low-volatile components of the coagulation bath must be washed out of the fibres first. In case of hyaluronan spinning, acid coagulation baths are most often used, in which acid hydrolysis of hyaluronan chains occurs and hyaluronan salts are converted to an acidic form. Non-woven fabrics from hyaluronan are not prepared directly by wet spinning, but the obtained fibres must be processed into their form in further steps by one of the known procedures, typically wet or dry way of the production of non-woven fabrics.

Due to the aforementioned disadvantages of wet spinning, dry spinning or even better melt spinning is preferred when spinning polymers. The principle of melt spinning is the extrusion of the polymer melt into a cooling gas, where the melt stream solidifies into fibres. Therefore, neither a coagulation bath nor a solvent is present here, and the solid fibre is formed from the liquid state very quickly, since the process is not slowed down by mass transfer. However, hyaluronic acid cannot be melted, because due to the presence of strong intermolecular bonds between its chains, it degrades, when heated, before it starts to melt. The same applies to most of its derivatives.

Only WO 2005/028632 A2 discloses the preparation of hyaluronan esters in which aliphatic acyls disrupt the intermolecular bonds to such an extent that the hyaluronan derivative becomes meltable. The document WO 2017/039335 A1 discloses the preparation of hyaluronan fibres using a melt spinning device, where the fibre is formed from hyaluronan comprising 5 to 20% of water at 150 to 200° C. and is subsequently cured in mixtures of water and ethanol, so it is not a true melt spinning.

The principle of dry spinning is the extrusion of a polymer solution into a drying gas, in which the solution is dried into fibres. There is a one-way transfer of mass, solvent from the solution to the drying gas, and therefore dry spinning is between the wet spinning and the melt spinning in terms of difficulty and speed of production. Dry spinning of hyaluronan is not known yet. Snetkov in his comprehensive article (Snetkov, P., Morozkina, S., Uspenskaya, M., & Olekhnovich, R. (2019). Hyaluronan-Based Nanofibers: Fabrication, Characterization and Application. Polymers, 11(12), 2036) reported that dry spinning of hyaluronan is difficult to be carried out due to the solubility of hyaluronan in water and could probably be carried out for hydrophobic hyaluronan derivatives that are soluble in easily evaporable organic solvents.

The document WO 89/10941 A1 refers to a preparation and processing of crosslinked acidic polysaccharide esters including hyaluronan and as one of the options for spinning thereof mentions the dissolution of the crosslinked polysaccharide in an organic solvent and—if the solvent used does not have a very high boiling point—removal of the solvent by a dry spinning process. In the examples, however, only the wet spinning of cross-linked carboxymethyl cellulose is described.

The document JP 2007-262595 A, which is the closest to dry spinning of hyaluronan, discloses preparation of an ultrathin filament from crosslinked hyaluronan, which is prepared by extruding a crosslinked gel and its subsequent mechanical stretching and pulling in an oven.

The document WO 2018/235745 A1 describes the preparation of non-woven fabrics by extruding a heated polymer solution that is captured in an air stream coming from a nozzle that is not in contact with the extrusion nozzle. The invention discourages the arrangement where the air flows around the extrusion nozzle. The air carries the solution to the collector, where it is deposited in the form of partially dried fibres that need to be dried by lyophilization, which in the examples takes 72 hours, which significantly complicates and prolongs the process. In addition, the document mainly focuses on the spinning of gelatin, for which there are all examples, hyaluronan is only mentioned, without any parameters.

Centrifugal solution spinning is based on a similar principle to dry spinning. The principle is the extrusion of the solution by centrifugal force through the openings in the walls of a rotating container, the stream of the extruded solution is then drawn into the form of a fibre by the action of centrifugal force and frictional force caused by air resistance. The document US 2013/0312638 A1 discloses a device for centrifugal spinning of polymers, but does not give any examples or specific parameters for hyaluronan. The document WO 2014/127099 A2 then states that centrifugal spinning in a classical arrangement is not suitable for solutions with slowly evaporating solvents (such as water) and recommends for them a technology called "immersed rotary jet spinning", which differs from the classical centrifugal spinning by bath of the liquid into which the fibres are deposited. So, it is a kind of combination of centrifugal and wet spinning. Even this document only mentions hyaluronan and does not give any examples or parameters. Chantre in his publication describes the use of "immersed rotary jet spinning" technology, directly for spinning hyaluronan (Chantre, C. O., Gonzalez, G. M., Ahn, S., Cera, L., Campbell, P. H., Hoerstrup, S. P., & Parker, K. K. (2019). Porous Biomimetic Hyaluronic Acid and Extracellular Matrix Protein Nanofiber Scaffolds for Accelerated Cutaneous Tissue Repair. ACS Applied Materials & Interfaces, 11(49), 45498-45510).

The document CN 110424059 A recommends the addition of another polymer (e.g., polyethylene glycol or polyvinyl alcohol) for spinning biopolymers by centrifugal spinning, similarly to the case of electrospinning.

A relatively new polymer solution spinning technology first described by Medeiros in 2009 (Medeiros, E. S., Glenn, G. M., Klamczynski, A. P., Orts, W. J., & Mattoso, L. H. C.

(2009). Solution blow spinning: A new method to produce micro- and nanofibers from polymer solutions. Journal of Applied Polymer Science, 113(4), 2322-2330) is solution blowing, also called solution blow spinning. It is dry spinning, the principle of which is to dose a polymer solution into a stream of high-speed unheated gas through a needle located coaxially in an air nozzle. The publication describes the processing of synthetic polymers dissolved in organic solvents into fibres with diameters from hundreds of nanometers to units of micrometers.

Document IN 201741017782 A discloses a simple device for solution blow spinning and lists hyaluronan derivatives in the list of spinnable materials, but does not specify any specific parameters for them or which derivatives they are.

SUMMARY OF THE INVENTION

The drawbacks and limitations of the technical solutions mentioned in the state of the art are solved by the invention of the method of the preparation of fibres, where fibres are based on hyaluronic acid and/or water-soluble metal or non-metal salt thereof or on the basis of water-soluble mixture of metal and/or non-metal salts of hyaluronic acid and/or on the basis of hyaluronic acid derivative, where the essence of a method based on the principle of dry spinning and/or solution blow spinning is to prepare a spinning solution comprising hyaluronic acid and/or a metal or non-metal salt thereof or a mixture of salts and/or a hyaluronic acid derivative, which is then spun by extrusion into a drying air stream and the fibres are deposited on a collector in the form of a non-woven fabric. Dry spinning may include, for example, solution blow spinning. The present invention is advantageous and differs significantly from the state of the art in that it allows simultaneously:

1. to spin pure hyaluronan without the addition of another polymer and using solvents acceptable in healthcare;
2. to spin hyaluronan without the use of a coagulation bath;
3. to deposit the fibres on a collector directly in the form of both a flat and a bulky non-woven fabric of hyaluronan, which can be removed from the collector as a finished product immediately once the spinning is completed;
4. to dry the fibres on the collector in the order of units of up to tens of seconds, preferably of up to 30 seconds.

The present invention differs from the experts' opinions in that it successfully uses the dry spinning principle to spin hyaluronan and its water-soluble derivatives.

The invention therefore refers to the method of preparation of fibres based on hyaluronic acid and/or a water-soluble metal or non-metal salt thereof or on the basis of a water-soluble mixture of metal and/or non-metal salts of hyaluronic acid and/or on the basis of hyaluronic acid derivative by the method of dry spinning and/or solution blow spinning, where a spinning solution of hyaluronic acid and/or a water-soluble metal or non-metal salt thereof or a water-soluble mixture of metal and/or non-metal salts of hyaluronic acid and/or hyaluronic acid derivative is prepared, containing 1 to 5% by weight of hyaluronic acid and/or its water-soluble metal or non-metal salt or a water-soluble mixture of metal and/or non-metal salts of hyaluronic acid and/or hyaluronic acid derivative, 28 to 54% by weight of organic solvent and 44 to 70% by weight of water and after the complete dissolution of the polymer, the spinning solution is extruded through at least one dispensing opening having the diameter from 80 to 410 μm in the rate from 0.001 to 1.6 mL/min into the drying air stream, thereby obtaining fibres that are carried onto the collector. The water-soluble metal or non-metal salt refers for example to a compound of alkali metal, for example $Na^+$, $K^+$, $Li^+$, or metals $Ag^+$, $Au^+$, respectively non-metal, for example $NH_4^+$. The water-soluble mixture of metal and/or non-metal salts of hyaluronic acid can include in addition to monovalent metals or non-metals, bi- or tri-valent metal or non-metal salt. The hyaluronic acid derivative is preferably selected from the group comprising hyaluronan chloramide, hyaluronan 3-(2-furanyl)acryloyl ester, tyramine hyaluronan, hyaluronan benzyl ester, hyaluronan ethyl ester and acylated derivatives of hyaluronan selected from the group comprising capronoyl, capryloyl, caprinoyl, lauroyl, myristoyl, palmitoyl, stearoyl, oleoyl hyaluronan.

The weight average molecular weight of hyaluronic acid and/or the water-soluble metal or non-metal salts thereof and/or the derivative thereof is preferably in the range from 90 kDa to 2.5 MDa.

In a preferred embodiment the organic solvent is selected from the group comprising methanol, tetrahydrofuran, methyl acetate, methyl ethylketone, 1,2-dimethoxyethane, acetonitrile, isopropylalcohol, 1-propanol, ethanol and acetone, preferably isopropylalcohol in the amount from 40 to 45% by weight.

The spinning solution is preferably prepared first by dispersing hyaluronic acid and/or a water-soluble metal or non-metal salt thereof or a water-soluble mixture of metal and/or non-metal salts of hyaluronic acid and/or a hyaluronic acid derivative in an organic solvent, water is added to the resulting dispersion with thorough mixing, and then the solution is stirred for 1 to 24 hours at temperature 20 to 30° C. until the polymer is completely dissolved. The prepared spinning solution is for example filled into a cartridge, which is sealed and connected to compressed air with an overpressure of +5 to +7 bar for 1 to 8 hours in order to dissolve the gas bubbles.

In another preferred embodiment, cooler air flows around the outlet opening for dispensing the solution, which air carries the spinning solution into a stream of warmer drying air. The drying air temperature is preferably 15 to 600° C., more preferably 15 to 350° C., and the absolute humidity of the drying air is preferably 0 to 14 g/$m^3$, more preferably 0 to 2 g/$m^3$, and the drying air flow rate is preferably 1.6 to 315 m/s, more preferably 5 to 260 m/s. Preferably, the drying air can be directed by one or more hollow cylinders.

In another preferred embodiment, the collector is covered with an inert material with a low surface energy, for example with polytetrafluoroethylene or polyethylene, from which the fibres are easily removed, or it is covered with a textile, for example polyester knitted fabric, on which the fibres are deposited and which remains a part of the final product.

Preferably, the fibres have a diameter of 100 nm to 100 μm and form a non-woven fabric on the collector, having an area weight 0.1 to 120 g/$m^2$.

In another embodiment, the spinning solution is a solution of hyaluronan 3-(2-furanyl)acryloyl ester, or a mixture of hyaluronic acid or a water-soluble salt thereof and hyaluronan 3-(2-furanyl)acryloyl ester, with the total concentration of the mixture of 1 to 5% by weight and the resulting fibres in the form of a non-woven fabric are subsequently cross-linked by radiation with a wavelength in the range from 280 to 750 nm, preferably 302 nm, for 2-60 minutes, wherein the substitution degree of hyaluronan with 3-(2-furanyl)acryloyl is in the range from 0.1 to 20%, and the proportion of hyaluronan 3-(2-furanyl)acryloyl ester in the mixture with the native HA is at least 0.1%, preferably 0.1-75%.

In any of the above-mentioned embodiments, the spinning solution can preferably contain an auxiliary polymer, such as carboxymethyl cellulose or oxycellulose, and/or a pharmaceutically and/or cosmetically acceptable low molecular weight substance that can be dissolved or dispersed in the solvent mixture used, selected from the group comprising antibacterial agents, e.g., octenidine dihydrochloride or carbethopendecinium bromide, antivirals, e.g., acyclovir, antifungals, e.g., clotrimazole or terbinafine, drugs, e.g., lidocaine hydrochloride, vitamins, e.g., riboflavin, plant extracts, e.g., bisabolol, surfactants, e.g., polysorbate 80, peptides, e.g., antimicrobial peptides, e.g., cathelicidine LL-37, pexiganan MSI-78, WR-12, wound healing promoting peptides, e.g., dalargin, TP-508, biotin-GHK, hormonal peptides, e.g., lysipressin, terlipressin, dyes, e.g., Patent Blue VF.

The method according to the invention is carried out first by preparing a spinning solution of hyaluronic acid and/or a water-soluble metal or non-metal salt or a water-soluble mixture of metal and/or non-metal salts of hyaluronic acid and/or hyaluronic acid derivative containing 1 to 5% by weight of hyaluronic acid and/or a metal or non-metal salt thereof or a water-soluble mixture of metal and/or non-metal salts of hyaluronic acid and/or hyaluronic acid derivative, 28 to 54% by weight of an organic solvent and 44 to 70% by weight of water, preferably 1 to 5% by weight of hyaluronic acid and/or a metal or non-metal salt thereof or a mixture of metal and/or non-metal salts of hyaluronic acid and/or a derivative thereof, 40 to 45% by weight of 2-propanol and 52 to 59% by weight of water.

The initial hyaluronic acid and/or the water-soluble metal or non-metal salt thereof and/or the derivative thereof has a weight average molecular weight (determined by the method of Size Exclusion Chromatography coupled to Multi-Angle Laser Light Scattering, SEC-MALLS) 90 kDa to 2.5 MDa, preferably 1.00 to 2.5 MDa. For example, the weight average molecular weight of native hyaluronic acid and/or a metal or non-metal salt thereof is preferably in the range from 1.0 MDa to 2.5 MDa, the weight average molecular weight of lauroyl hyaluronan is preferably 100 kDa to 1.00 MDa. The molecular weights used must be adapted to the concentration of the polymer in the spinning solution to achieve its optimal viscosity, for higher molecular weights lower concentrations must be chosen and vice versa. If the viscosity of the spinning solution is too high, there is no effective elongation of the resulting fibre and the extruded solution stream breaks instead. If the viscosity of the spinning solution is too low, after being extruded by the dispensing opening the solution stream breaks up into drops.

If a hyaluronic acid derivative is used, e.g., lauroyl hyaluronan, it is defined in the examples by the content of the bound fatty acid, which indicates the mass proportion of the bound fatty acid in the total derivative weight.

In a preferred embodiment, the spinning solution is a solution of a hyaluronic acid derivative, which is hyaluronan chloramide, or a mixture of a hyaluronic acid derivative, which is hyaluronan chloramide, and native hyaluronic acid, wherein the substitution degree of hyaluronan chloramide is in the range from 0.1% to 100%, preferably 50 to 100%.

The procedure for preparing the spinning solution is preferably such that first hyaluronic acid and/or the metal or non-metal salt thereof or the water-soluble mixture of metal and/or non-metal salts of hyaluronic acid and/or hyaluronic acid derivative is dispersed in an organic solvent, then water is added with thorough mixing and the solution is stirred for 1 to 24 hours at the temperature 20 to 30° C. until the polymer is completely dissolved. The spinning solution is then filled into the cartridge of a pneumatic dosing device (working on the principle of extruding the solution from the storage cartridge with compressed air, an example of such a dosing device is the Vieweg DC 1200), the cartridge is sealed and connected to the compressed air with an overpressure of +5 to +7 bar for 1 to 8 hours until the gas bubbles dissolve.

The spinning solution is extruded by an extrusion part with at least one dispensing opening with an internal diameter of 80 to 410 micrometers, preferably 100 to 210 micrometers. The term extrusion part in this description preferably refers to a conventional extrusion needle with a blunt end and with 1 to 4 capillaries, which may be straight or bent to allow their better positioning in the air stream, or a conical extrusion needle, the internal diameter of which gradually decreases up to the dispensing opening, thanks to which it can dispense viscous solutions at a lower pressure, or a nozzle containing more than one dispensing opening, preferably more than 10, more preferably more than 50 dispensing openings arranged for example in a row.

The spinning solution is extruded from the dispensing opening with a rate from 0.001 30 to 1.6 mL/min. At a lower dosing rate, drawing and air-drying of the fibres are both more efficient and the fibres fall onto the collector dried better, but at the same time the spinning solution in the extrusion part is more heated and especially when the extrusion part is flown around with air of a higher temperature, there is a risk of drying the solution and clogging the dispensing opening.

The spinning solution is extruded from the dispensing opening into a stream of drying air that flows around the extrusion part. The stream of drying air draws the extruded spinning solution into a fibre shape, speeds up the evaporation of the solvent from the spinning solution and drifts the resulting fibres onto the collector.

In a preferred embodiment of the invention, the extrusion part is flown around by a smaller amount of cooler air, which carries the spinning solution into a stream of a larger amount of warmer drying air, wherein this embodiment prevents overheating of the spinning solution already in the extrusion part.

The temperature of the drying air is 15 to 600° C., preferably 15 to 350° C., the absolute humidity of the drying air is 0 to 14 $g/m^3$, preferably 0 to 2 $g/m^3$, the drying air flow rate is 1.6 to 315 m/s, preferably 5 to 260 m/s. The air flow rate at the nozzle outlet depends on the combination of the nozzle cross-section and the volumetric flow rate. In general, when using a higher drying air flow rate, a lower drying air temperature can be used to effectively dry the fibres and vice versa, because the faster flowing drying air draws the resulting fibre more effectively into a smaller diameter fibre from which the drying air more easily removes solvents. Similarly, the use of a dispensing opening with a smaller internal diameter supports the formation of a fibre with a smaller diameter.

In a preferred embodiment of the invention, the drying air carrying the resulting fibre is directed by one or more hollow cylinders, which prevent the expansion of the drying air stream and its mixing with the surrounding air, thereby reducing its speed and temperature.

The fibres are deposited in the form of a non-woven fabric on a collector with a shape of a cylinder, bars, belt or board. The collector is immobile or preferably mobile, such as a cylinder rotating around its axis or a belt rewound from cylinder to cylinder. The surface of the collector is preferably covered with an inert material with a low surface energy, for example with polytetrafluoroethylene or polyethylene, from which the fibres can be easily removed. The collector's distance from the dispensing opening is preferably in the range from 5 cm to 140 cm. In another embodiment of the invention, the collector is covered with a fabric or a film, for example polyester or polyamide fabric or film, which forms one of the layers of the final product, and the prepared fibres are applied directly thereon as another layer.

In a preferred embodiment of the invention the arrangement of the collector is such that the fibres deposited on the collector hang most of their length in the air and can thus dry more effectively. In this embodiment, the collector is formed for example by bars or is covered with a fabric with larger meshes.

In another preferred embodiment of the invention the collector with the shape of a cylinder rotating around its axis can be moved along this axis, so that the fibres gradually fall on its entire surface in a uniformly thick layer.

In another preferred embodiment of the invention the collector is an object on the surface of which a layer of a non-woven fabric is formed and then together with the object it forms the final product. It's for example an implantable medical device (pacemaker, joint . . . ) covered with a biocompatible or antimicrobial layer.

Further, the subject of the invention is a two-dimensional or three-dimensional material made of microfibres or nanofibres prepared in the manner described above. The non-woven fabric of the invention has preferably an area weight from 0.1 to 120 $g/m^2$ and is made of fibres with a diameter in the range from 100 nm to 100 micrometers. Non-woven fabrics of higher area weights, approx. from 5 $g/m^2$, can be used as self-supporting two-dimensional materials, non-woven fabrics of lower area weights are not rigid enough to maintain the shape of a flat structure, and after being removed from the collector, they self-fold into a three-dimensional structure similar to cotton wool.

As mentioned above, the amounts of solvents contained in the fibres falling on the collector can be influenced by the parameters selection (in particular, the rate of spinning solution dosing, the diameter of the dispensing opening, the drying air temperature and the drying air flow rate). For obtaining high-quality fibres and the non-woven fabric formed by them, preferably such combination of parameters is selected, that the fibres fall on the collector dry enough (i.e., with such a low residual content of solvents) to retain the shape of the fibre and to complete drying quickly enough (preferably within a few tens of seconds at most) to prevent a layer of gel growing on the collector. If not completely dried fibres fall on each other, they coalesce in the places where they cross each other. In a preferred embodiment of the invention, the fibres fall on the collector dry enough, so their coalescence does not occur. The resulting non-woven fabric is characterized by a lower volumetric mass. In another preferred embodiment of the invention, the fibres fall on the collector dry enough to directly form a three-dimensional, cotton wool-like formation, so it is not necessary to assemble such a formation from thin two-dimensional layers.

Furthermore, the subject of the invention is a device for the preparation of two-dimensional or three-dimensional materials from microfibres or nanofibres, which includes an extrusion part containing a pass-through channel, which has an inlet opening for feeding the spinning solution and at least one dispensing opening for dispensing the spinning solution and an air nozzle, the air outlet opening of which is arranged to direct the exiting air to an area surrounding the dispensing opening of the extrusion part parallel to the axis of the dispensing opening of the extrusion part. In a preferred embodiment the device contains a source of drying air, air nozzle, device for dosing of the spinning solution, extrusion part, e.g., a extrusion needle, positioned coaxially with the air nozzle, and a collector. The collector is arranged at a distance from the extrusion part and the dispensing opening of the extrusion part is facing the collecting surface of the collector.

In another preferred embodiment of the invention, the stream of the drying air carrying the stream of the spinning solution is directed through a defined space, which prevents mixing with the surrounding air, by means of a focusing part arranged between the collector and the dispensing opening of the extrusion part and containing a pass-through cavity, the axis of which is identical to the axis of the dispensing opening. The outlet opening of the air nozzle is preferably annular and arranged coaxially with the dispensing opening of the extrusion part and/or the outlet opening of the air nozzle is arranged farther away from the collector than the dispensing opening.

In other embodiments, the device includes a compressor for feeding air to the air nozzle and/or the device includes a heating element for heating the air fed to the air nozzle.

In a preferred embodiment of the invention, there are multiple sources of drying air of different temperatures. The device may include additional nozzles that are arranged to direct the additional air stream into the air stream from the air nozzle at an angle 30 to 60°.

In another preferred embodiment, the device includes at least one panel arranged between the outlet opening of the air nozzle and the outlet opening of the additional nozzle.

The prepared two-dimensional and three-dimensional fibrous materials can be used in medicine as covers or fillings for wound treatment.

EXAMPLES

Figure 1:
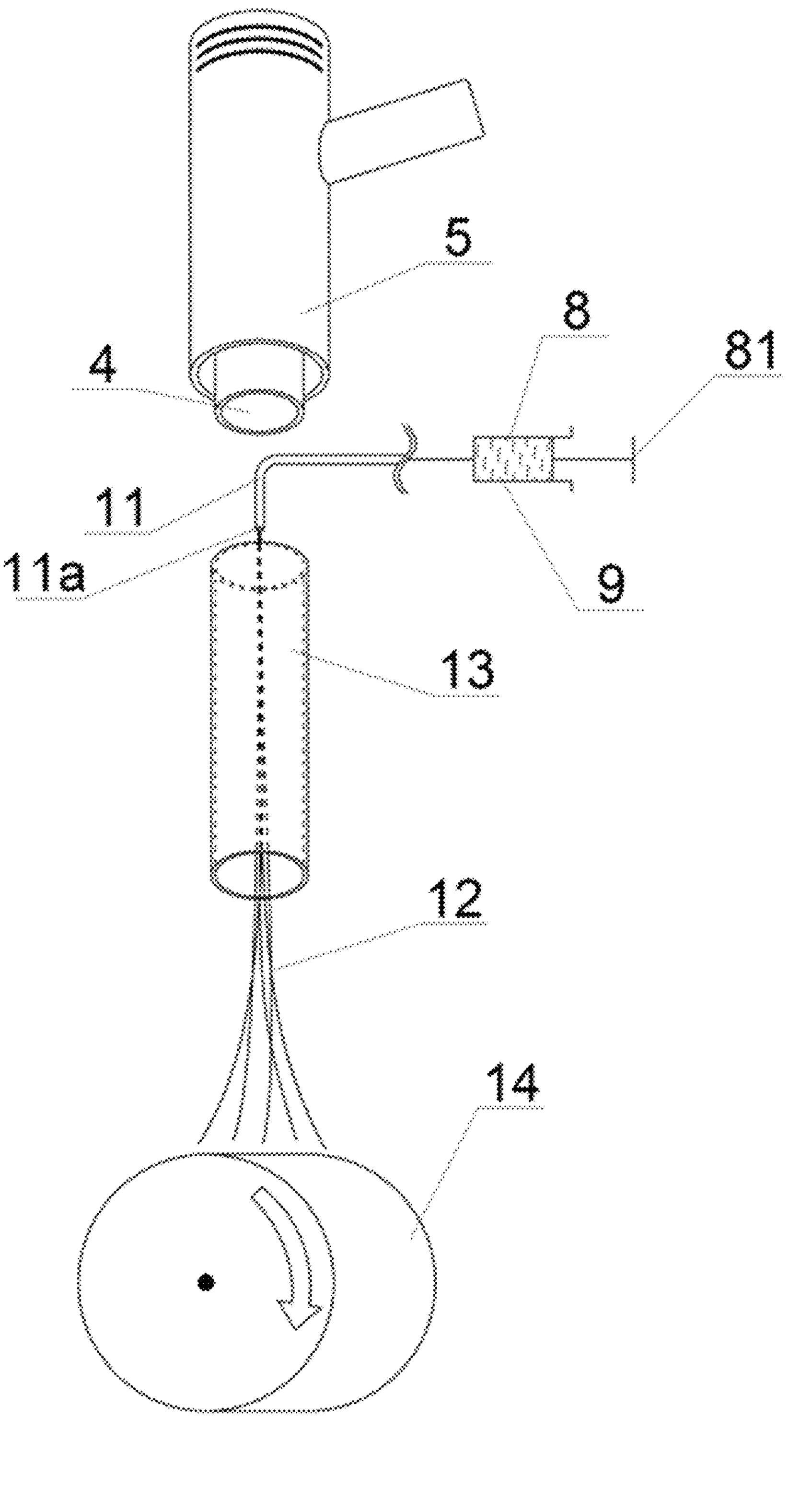
FIG. 1 shows a first exemplary embodiment of a device with a heat gun as an air source.

The device according to the present invention thus comprises an extrusion part 11 comprising a pass-through channel having an inlet opening for feeding a spinning solution 9 and a dispensing opening 11*a* for discharging of the spinning solution, and an air nozzle 5, having an outlet opening 6 for the exit of air which is arranged for directing of the exiting air into the region surrounding the dispensing opening 11*a* of the extrusion part 11 in parallel to the axis of the dispensing opening 11*a* of the extrusion part 11. Furthermore, the device preferably comprises a collector 14 arranged in a certain distance from the extrusion part 11, wherein the dispensing opening 11*a* of the extrusion part 11 faces the collecting surface of the collector 14.

In a preferred embodiment, the device comprises a focusing part 13 arranged between the collector 14 and the dispensing opening 11*a* of the extrusion part 11, said focusing part 13 comprising a pass-through cavity, the axis of which being identical to the axis of the dispensing opening 11*a*.

An outlet opening 4 of the air nozzle 5 is preferably annular and arranged coaxially with the dispensing opening 11*a* of the extrusion part 11 and/or the outlet opening 4 of the air nozzle 5 is arranged farther from the collector 14 than the dispensing opening 11*a*.

The device may comprise a compressor 1 for feeding the air into the air nozzle 5.

In another preferred embodiment, the device also comprises a heating element 2 for heating the air fed into the air nozzle 5.

In another preferred embodiment, the device comprises additional air nozzles 5*a*, 5*b* which are arranged for directing an additional air stream into the air stream of the air nozzle 5 in an angle of 30° to 60°. The device can further comprise at least one focusing panel 7 arranged between the outlet opening 4 of the air nozzle 5 and an outlet opening 4*a*, 4*b* of the additional air nozzles 5*a*, 5*b*.

FIG. 1 shows schematically the first embodiment of the device for the production of two-dimensional or three-dimensional fibre materials from microfibres or nanofibres, wherein the device comprises an extrusion part 11 in the form of an extrusion needle through which a pass-through channel extends, said pass-through channel comprising a feeding opening and a dispensing opening 11*a*. The extrusion part 11 is adapted for a fluid connection with a dosing device 8 on the side of the feeding opening, in this case in the form of a cartouche with a piston 81.

The pass-through channel has a diameter of 80 to 410 micrometres, preferably 100 to 210 micrometres, at least in the region of the dispensing opening 11*a*.

The device further comprises an air nozzle 5, here in the form of a hot-air pistol. The air nozzle 5 has an outlet opening 4 which is directed and adapted for directing the hot air stream such that it flows around the extrusion part 11 in parallel to the direction of the exit of the spun solution from the dispensing opening 11*a* of the extrusion part 11. To this end, the air nozzle 5 is arranged so that the axis of its outlet opening 4 corresponds to the axis of the dispensing opening 11*a* of the extrusion part 11.

The device further comprises a collector 14 for depositing the produced fibres, in this case in the form of a rotatably arranged cylinder, wherein the dispensing opening 11*a* of the extrusion part 11 faces the depositing surface of the collector 14.

A focusing part 13 having a pass-through cavity is arranged between the collector 14 and the dispensing opening 11*a* of the extrusion part 11, wherein the axis of said pass-through cavity corresponds to the axis of the dispensing opening 11*a*. The pass-through cavity of the focusing part 13 is cylindrical.

By means of the piston 81, a polymer solution 9 is extruded from the dosing device 8 by means of a bent extrusion needle forming an extrusion part 11 and being arranged coaxially under the outlet opening 4 of the air nozzle 5. The resulting fibres are led through the focusing part 13 onto the collector 14.

Figure 2:
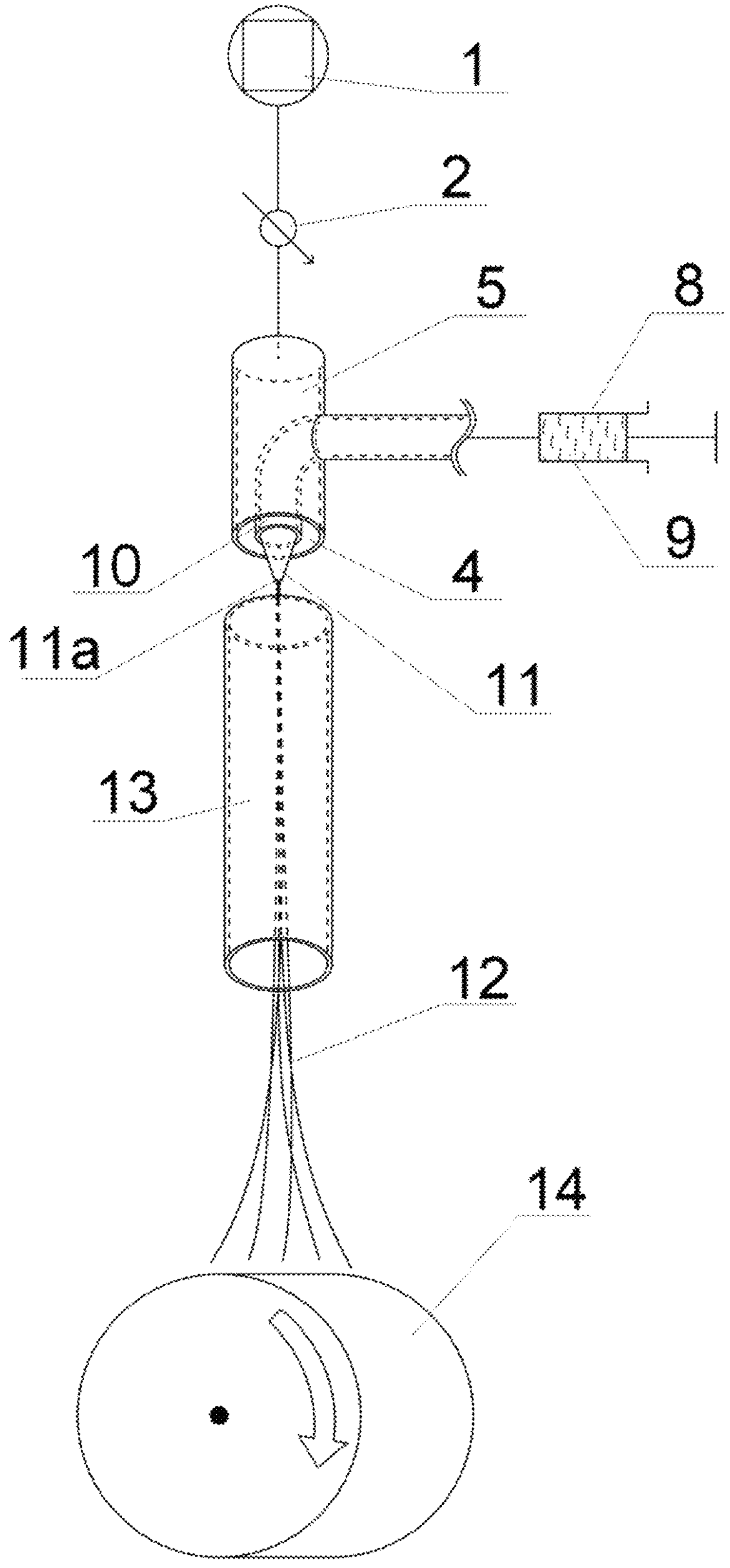
FIG. 2 shows a second exemplary embodiment of a device with a compressor as an air source and with an extrusion conical needle coaxially located in the center of the air nozzle.

FIG. 2 shows schematically another embodiment of the device for the production of two-dimensional or three-dimensional fibre materials from microfibres or nanofibres which differs from the device of FIG. 1 particularly in that the extrusion part 11 is partially housed inside the air nozzle 5 and at the same time protrudes from the air nozzle 5 with the part that comprises the dispensing opening 11*a*. Furthermore, the device of FIG. 2 is supplemented with a compressor 1 which is fluidly interconnected with the air nozzle 5 for feeding an air stream to the air nozzle 5. A heating element 2 for heating the air fed to the air nozzle 5 is arranged in a piping interconnecting the compressor 1 and the air nozzle 5.

The polymer solution 9 is brought from the dosing device 8 to the extrusion part 11 which comprises a tube 10 followed by an extrusion needle 11. The air stream generated by the compressor 1 is heated by the heating element 2 and exits the air nozzle 5 through an outlet opening 4 having a shape of annulus, the dispensing opening 11*a* of the extrusion needle 11 being coaxially arranged therewith. The resulting fibres 12 are led by the focusing cylinder 13 onto the collector 14.

Figure 3:
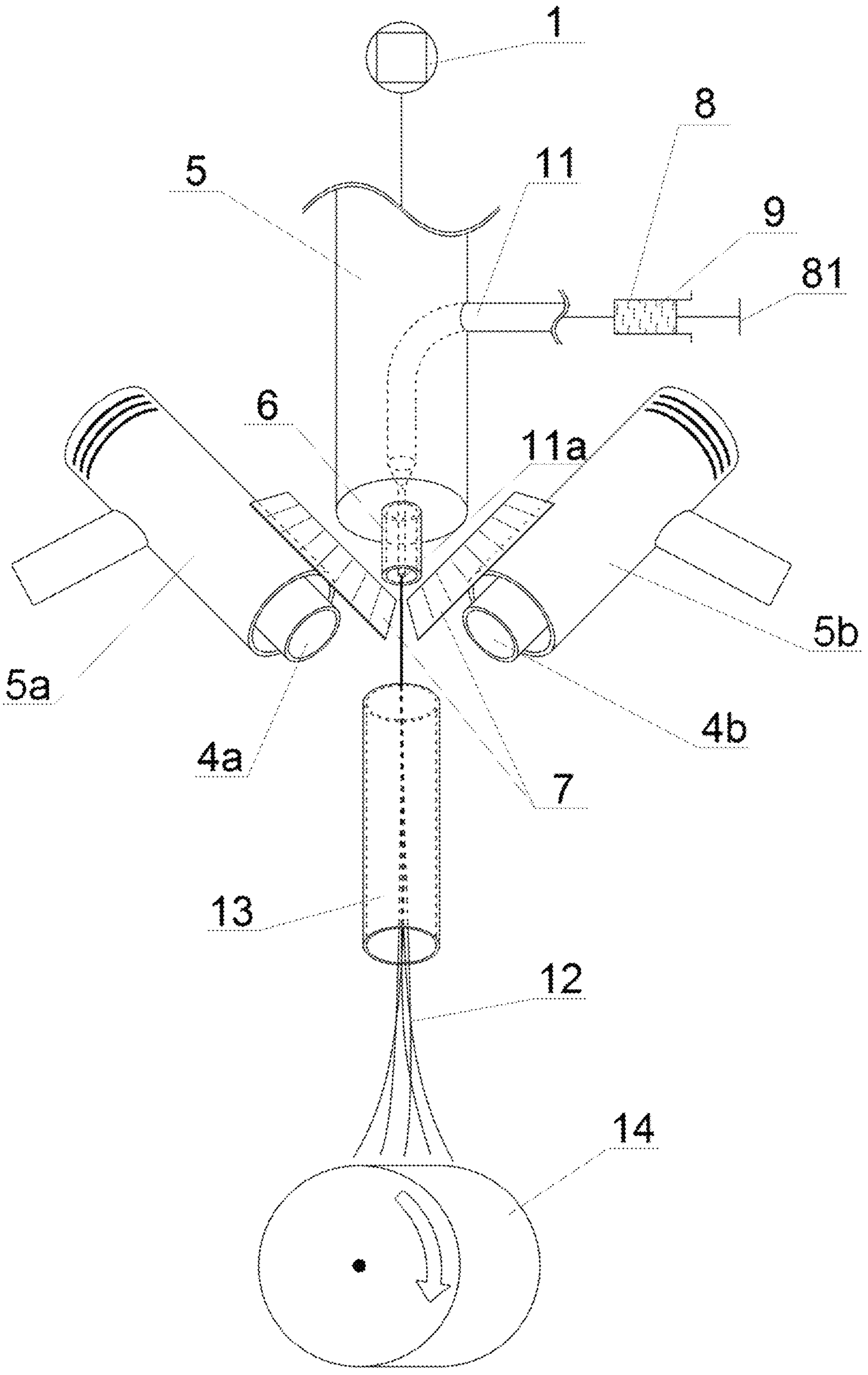
FIG. 3 shows a third exemplary embodiment of a device with a combination of non-heated and heated air.

FIG. 3 shows schematically the third embodiment of the device for the production of two-dimensional or three-dimensional fibre materials from microfibres or nanofibres according to the invention with a combination of non-heated and heated air.

The device of FIG. 3 differs from the device of FIG. 2 particularly in that the dispensing opening 11*a* of the extrusion part 11 is arranged substantially in the same plane as the outlet opening of the air nozzle 5 and that outlet openings 4*a*, 4*b* of additional air nozzles 5*a*, 5*b* are directed to the region between the dispensing opening 11*a* of the extrusion part 11 and the inlet opening of the pass-through cavity of the focusing part 13.

The axes of the outlet openings 4*a*, 4*b* of the additional air nozzles 5*a*, 5*b* intersect the axis of the dispensing opening 11*a* of the extrusion part 11 and form an angle of 30° to 60° with said axis, wherein a focusing panel 7 is always arranged between the air nozzle 5 and the additional nozzle 5*a*, 5*b*, said focusing panel 7 being made of e.g. sheet metal. Instead of focusing panels 7, e.g. a funnel can be used for focusing.

The dosing device 8 extrudes the polymer solution 9 through a straight extrusion needle forming the extrusion part 11 arranged coaxially in the outlet cylinder 6 of the air nozzle 5, into which the air form the compressor 1 is fed. Said air brings the solution into a flow of warmer (heated) air exiting the outlet openings 4*a*, 4*b* of the additional air nozzles 5*a*, 5*b* and directed by two focusing panels 7. The resulting fibres 12 are led between the focusing panels 7 and further through the focusing cylinder 13 onto the collector 14.

Figure 4:
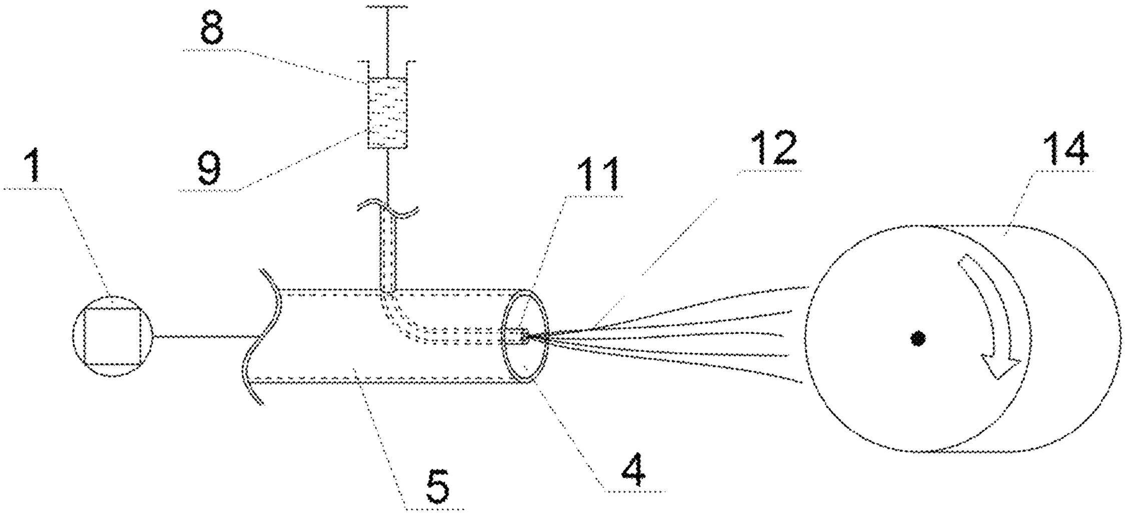
FIG. 4 shows the fourth exemplary embodiment of the device based on the principle of solution blow spinning technology.

FIG. 4 shows schematically the fourth embodiment of the device for the production of two-dimensional or three-dimensional fibre material according to the invention based on the solution blow spinning technology with a compressor 1 as a source of air and a narrow air nozzle 5 through which the air exits with a high velocity. The diameter of the air nozzle 5 is in the range of 2 to 4 mm, the velocity of the air is in the range of 50 to 350 m/s. The diameter of the needle is in the range of 80 to 210 micrometres. A dosing device 8 extrudes a polymer solution 9 through a bent extrusion needle forming an extrusion part 11 arranged coaxially in the outlet opening 4 of the air nozzle 5. The resulting fibres 12 are deposited on the collector 14.

Figure 5:
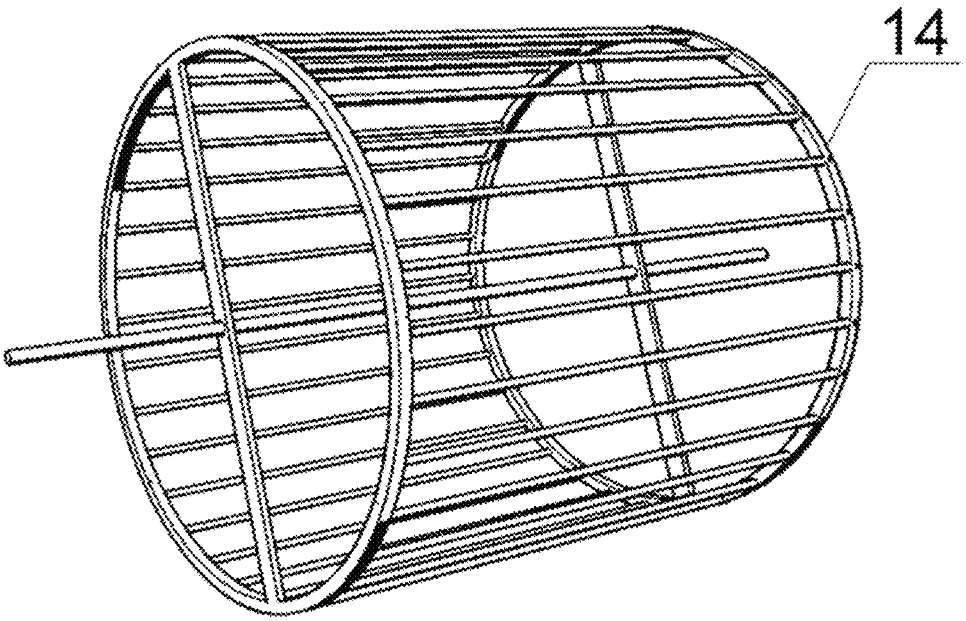
FIG. 5 shows a collector formed by bars.

FIG. 5 shows an example of the collector 14 in the form of a rotatably arranged cylindrical cage.

Figure 6A:
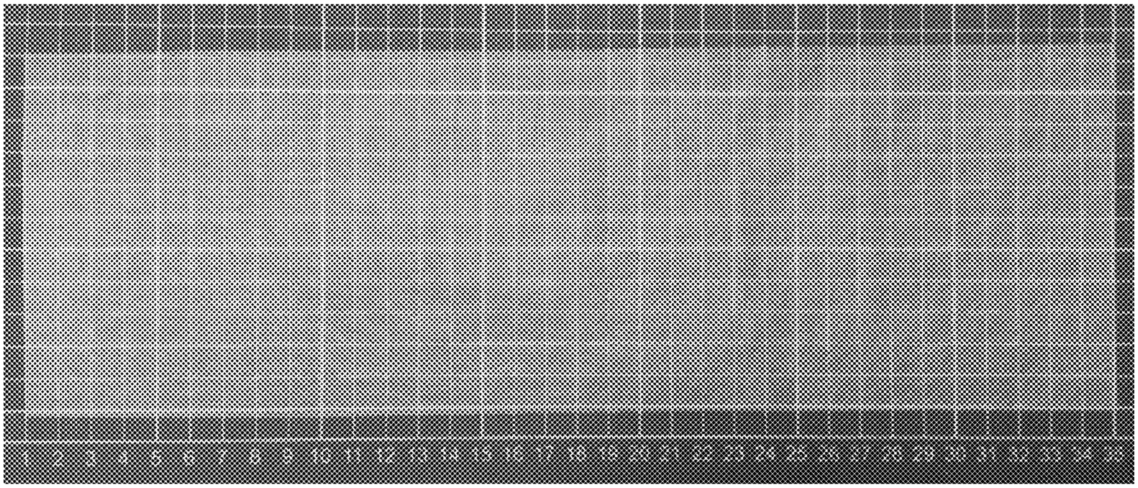
FIG. 6A shows a non-woven fabric made of sodium hyaluronan prepared according to Example 1.
Figure 6B:
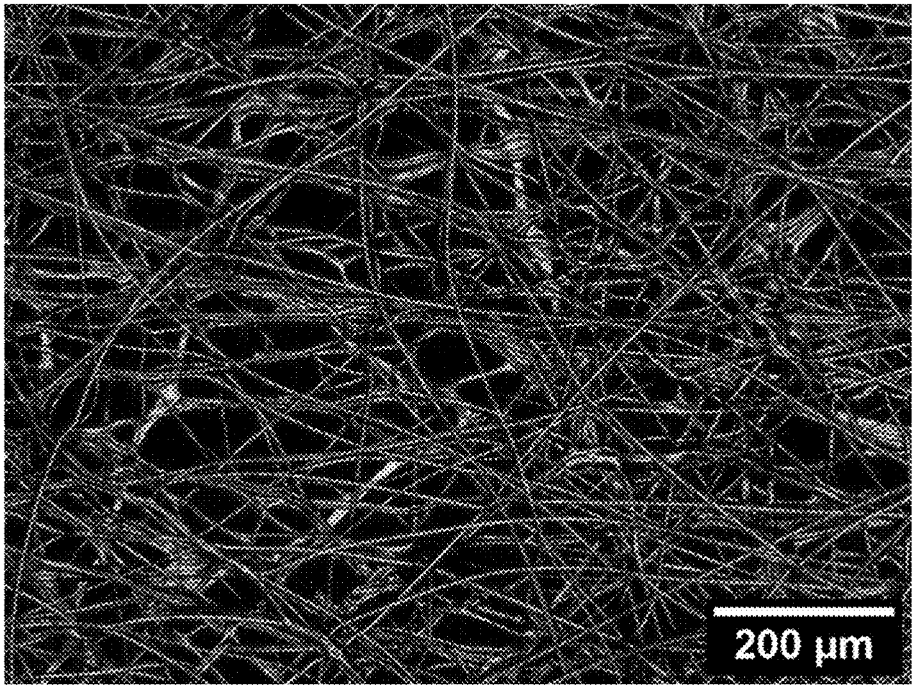
FIG. 6B shows the structure of the non-woven fabric made of sodium hyaluronan prepared according to Example 1.

Example 1: Non-Woven Fabric Made of Hyaluronan Prepared on a Device with Heat Gun 2 grams of sodium hyaluronan with weight average molecular weight 2 MDa are dispersed in 58.5 mL of 2-propanol. 56.0 mL of water is added to the resulting dispersion with thorough mixing, the solution is stirred until the polymer is completely dissolved for 5 hours at 25° C. resulting in 1.93% by weight of sodium hyaluronan. The spinning solution is then filled into the cartridge of the pneumatic dispensing device, the cartridge is sealed and connected to the compressed air of +6 bar for 4 hours until the gas bubbles dissolve. Subsequently, the spinning solution is spun on the device shown in FIG. 1. The spinning solution is extruded by a bent blunt extrusion needle of length 12.7 mm with an internal diameter of 160 micrometers with the rate of 0.3 mL/min. The extrusion needle is located coaxially under the point nozzle of the heat gun Wagner FURNO 750 so that the end of the extrusion needle is located 15 mm under the end of the point nozzle. The heat gun blows the drying air of temperature 190° C. and absolute humidity of 12 g/$m^3$ with the volume flow 280 L/min. The drying air is directed by a cylinder located coaxially with the extrusion needle, this cylinder of the internal diameter 2.7 cm and length 21.5 cm starts at 1 mm under the end of the extrusion needle. The resulting fibres are carried by the air stream to the collector in the shape of a cylinder with a diameter of 15 cm rotating at the speed 2 revolutions per minute located 115 cm under the extrusion needle. The surface of the collector is covered with polytetrafluoroethylene foil. The resulting non-woven fabric (FIG. 6A, raster scale 1×1 cm) has an area weight 7.6 g/$m^2$ and is made up of fibres with the diameter of 3-10 micrometers (FIG. 6B).

Example 2: Non-Woven Fabric Made of Hyaluronan Prepared on a Device with a Coaxial Air Nozzle 2 grams of sodium hyaluronan having the weight average molecular weight 1.68 MDa are dispersed in 58.5 mL of 2-propanol. 56.0 mL of water is added to the resulting dispersion with thorough mixing and the solution is stirred for 20 hours at 21° C. until the polymer is completely dissolved, resulting in 1.93% by weight solution of sodium hyaluronan. The spinning solution is then filled into the cartridge of the pneumatic dispensing device, the cartridge is sealed and connected to the compressed air of +6.8 bar for 3 hours until the gas bubbles dissolve. Subsequently, the spinning solution is spun on the device shown in FIG. 2. The spinning solution is extruded by a blunt extrusion needle of length 6.4 mm and internal diameter of 160 micrometers with the rate of 0.41 mL/min. The extrusion needle is located coaxially in the center of the air nozzle, the end of the needle is located 20 mm under the end of the air nozzle. The drying air flows from the air nozzle through an annular outlet with an internal diameter of 19 mm and an external diameter of 25 mm, the temperature of the drying air is 110° C., the absolute humidity is 0.2 g/$m^3$ and it has the volume flow 300 L/min. The drying air is directed by a cylinder located coaxially with the extrusion needle, this cylinder having the internal diameter of 3.7 cm and length of 17.5 cm starts at 1 mm under the end of the extrusion needle. The resulting fibres are carried by the air stream to the collector in the shape of a cylinder with a diameter of 15 cm rotating at speed of 3 revolutions per minute located 74 cm under the extrusion needle. The collector surface is covered with polyester non-reinforced knitted fabric Zuzana (manufacturer: SILK & PROGRESS). The resulting non-woven fabric has the area weight of 5.4 g/$m^2$ and is made of fibres having the diameter of 1-10 micrometers. The resulting non-woven fabric is removed from the collector together with the polyester knitted fabric, on which it is deposited, and can thus be used as the resulting two-layer product, or the non-woven fabric of polyester knitted fabric can be removed.

Figure 7A:
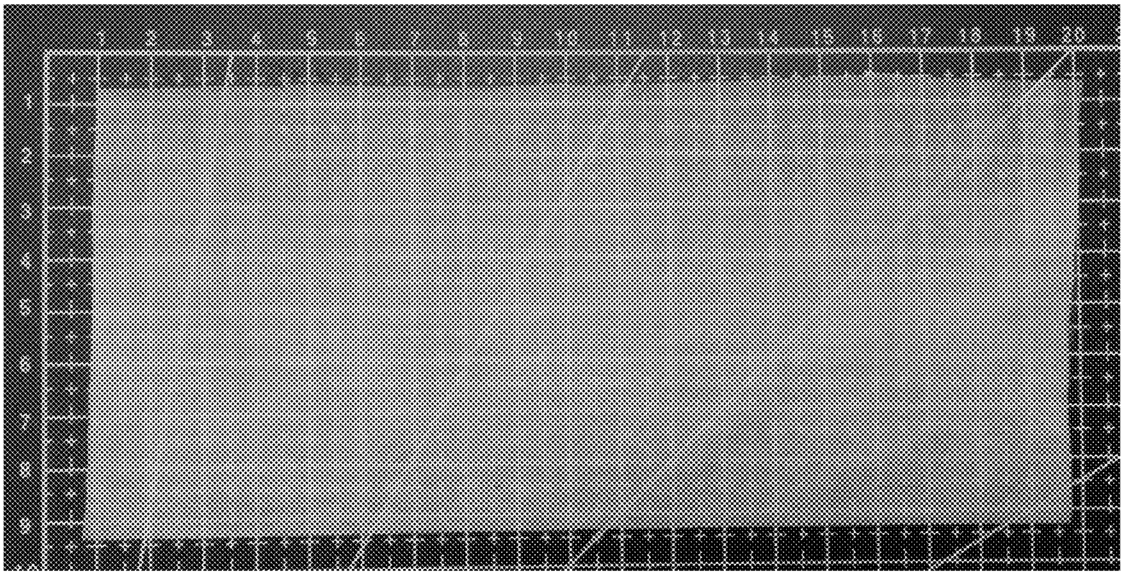
FIG. 7A shows a non-woven fabric made of sodium hyaluronan prepared according to Example 3.
Figure 7B:
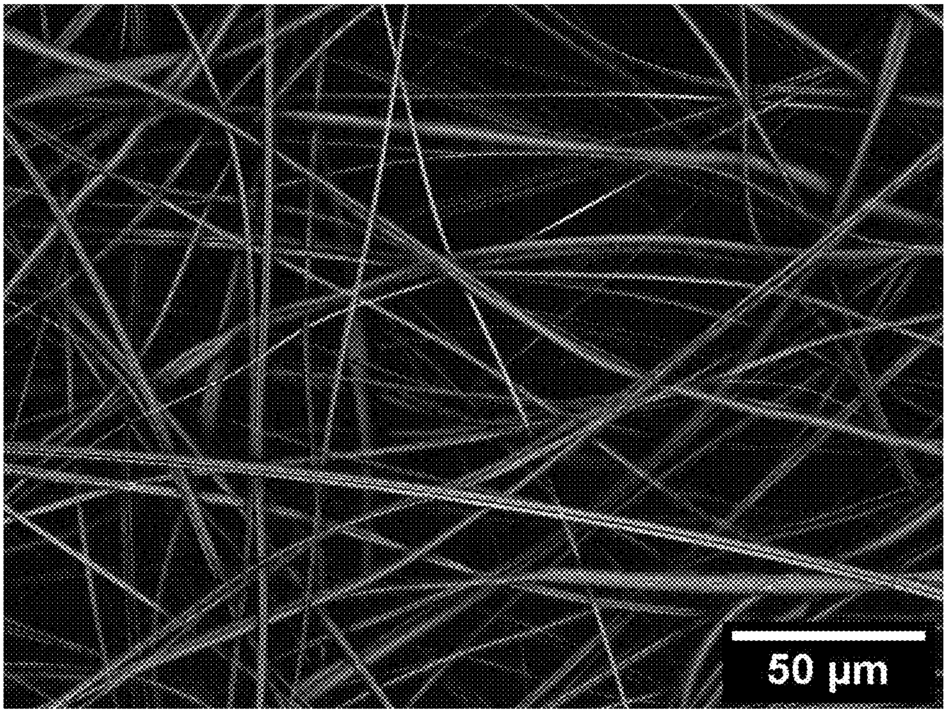
FIG. 7B shows the structure of the non-woven fabric made of sodium hyaluronan prepared according to Example 3.
Figure 7C:
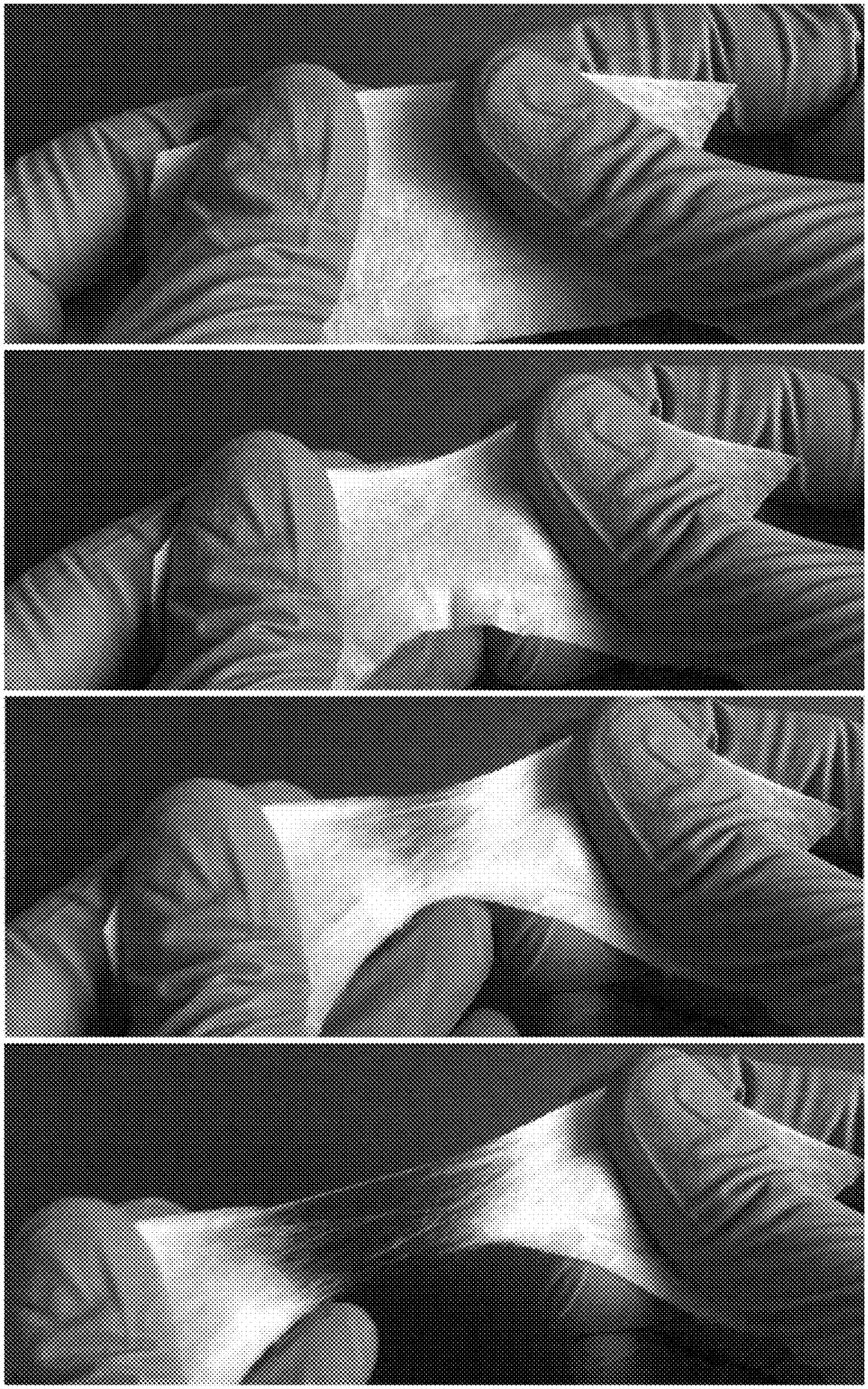
FIG. 7C shows the behavior of non-woven fabric made of sodium hyaluronan prepared according to Example 3 during tearing.

Example 3: Non-Woven Fabric Made of Hyaluronan Prepared on a Device with a Combination of Unheated and Heated Air 2 grams of sodium hyaluronan having the weight average molecular weight 2.31 MDa are dispersed in 58.5 mL of 2-propanol. 56.0 mL of water is added to the resulting dispersion with thorough mixing, the solution is stirred for 8 hours at 23° C. until the polymer is completely dissolved, resulting in a 1.93% by weight solution of sodium hyaluronan. The spinning solution is then filled into the cartridge of the pneumatic dispensing device, the cartridge is sealed and connected to the compressed air of +6.8 bar for 5 hours until the gas bubbles dissolve. Subsequently, the spinning solution is spun on the device shown in FIG. 3. The spinning solution is extruded by a blunt extrusion needle having the length of 12.7 mm internal diameter of 160 micrometers, with the rate 0.18 mL/min. The extrusion needle is located coaxially in the Luer Lock outlet of a common pneumatic dispenser cartridge having the volume of 55 mL, the end of the needle is located 1 mm under the end of the outlet from the cartridge. Through this outlet the air flows with the temperature of 22° C. and absolute humidity of 0.2 g/$m^3$ with the volume flow of 31 L/min. This air carries the stream of the spinning solution through a gap having the width of 9 mm between two metal sheets forming an angle with each other 90°, the gap between the plates is located 7 mm under the end of the extrusion needle. Under each sheet, a heat gun is placed, the gun being Wagner FURNO 750 with a wide nozzle so that the distance between the ends of the nozzles of both guns is 6 cm. Each gun blows the drying air of the temperature of 350° C. and absolute humidity of 11 g/$m^3$ with the volume flow of 190 L/min. The drying air is directed by two cylinders positioned coaxially with the extrusion needle, the first cylinder of the internal diameter of 4.1 cm and the length of 20 cm starts 6 cm under the end of the extrusion needle, the second cylinder of the internal diameter of 5.3 cm and the length of 40 cm starts 1 cm under the end of the first cylinder. The resulting fibres are carried by the air stream to the collector in the shape of a cylinder having a diameter of 15 cm rotating at the speed of 2 revolutions per minute and located 100 cm under the extrusion needle. The surface of the collector is covered with polytetrafluoroethylene foil. The resulting non-woven fabric (FIG. 7A, raster scale 1×1 cm) has the area weight of 13 g/$m^2$ and is made of mutually unfused fibres of diameter 1-6 micrometers (FIG. 7B), which is manifested by a characteristic tearing behavior, when the fibres slide over each other (FIG. 7C).

Figure 8A:
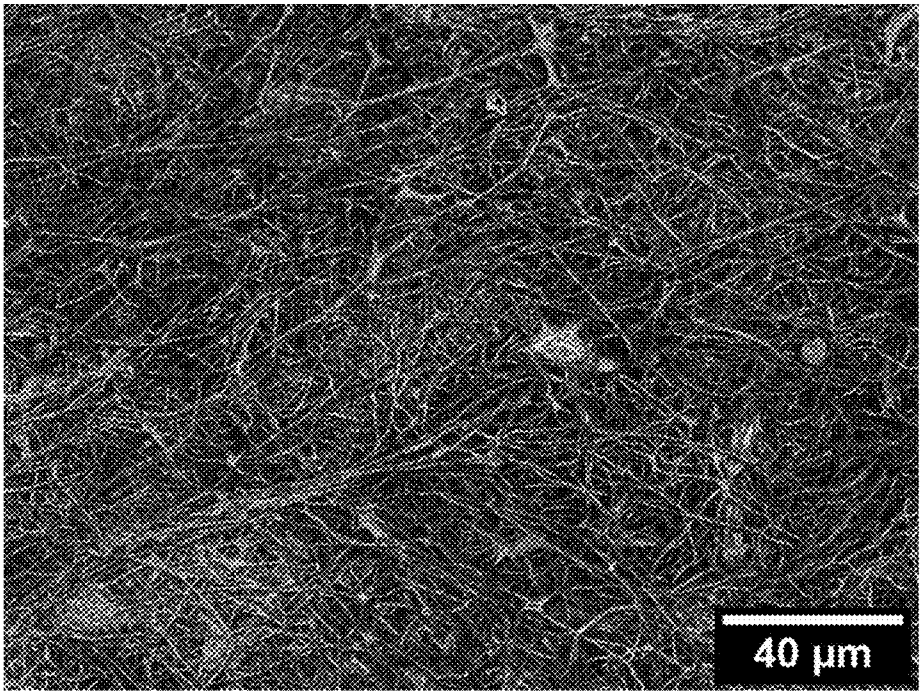
FIGS. 8A and 8B show a bulky fibrous structure made of sodium hyaluronan prepared according to Example 4, in FIG. 8A compressed into a compact structure, in FIG. 8B uncompressed, porous.
Figure 8B:
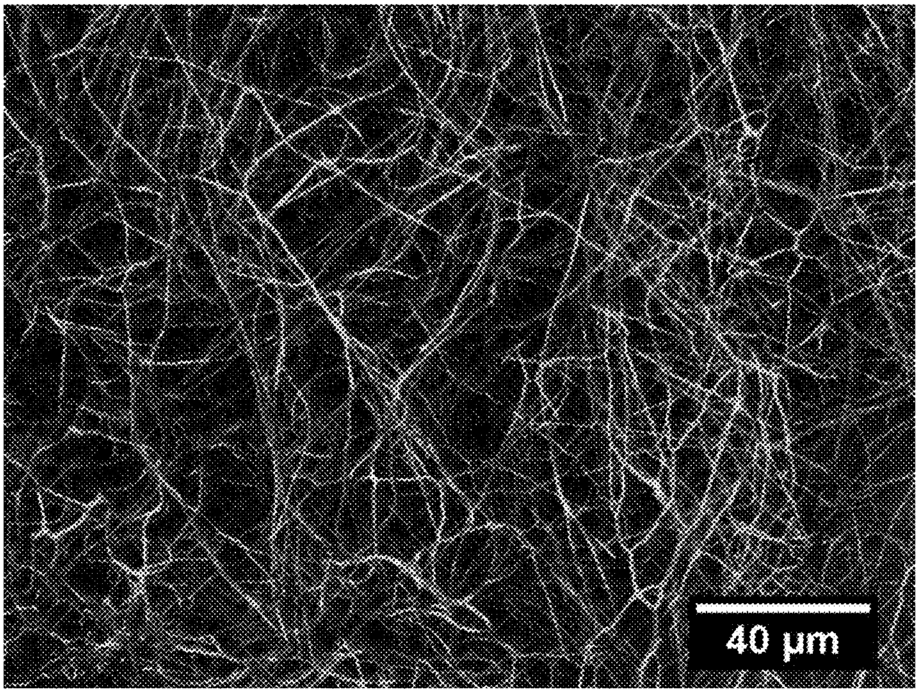

Example 4: Hyaluronan Nanofibres Prepared by the Method of Solution Blow Spinning 2 grams of sodium hyaluronan with the weight average molecular weight of 2 MDa are dispersed in 96.3 mL of 2-propanol. 75.4 mL of water is added to the resulting dispersion with thorough mixing, the solution is stirred for 5 hours at 21° C. until the polymer is completely dissolved, resulting in a 1.31% by weight solution of sodium hyaluronan. The spinning solution is then filled into the cartridge of the pneumatic dispensing device, the cartridge is sealed and connected to the compressed air of +5 bar for 1 hour until the gas bubbles dissolve. Subsequently, the spinning solution is spun on the device shown in FIG. 4. The spinning solution is extruded by a bent blunt extrusion needle of length of 12.7 mm having an internal diameter of 160 micrometers with the rate of 0.04 mL/min. The extrusion needle is located coaxially in an air nozzle formed by a polyamide tube of the internal diameter of 4 mm so that the end of the needle exceeds the tube by 2 mm. The air nozzle blows the drying air of the temperature of 22° C. and absolute humidity of 0.2 g/$m^3$ with the volume flow of 80 L/min. The resulting fibres are carried by the air stream to the collector in the shape of a cylinder with a diameter of 7 cm rotating at the speed of 90 revolutions per minute and located at a distance of 10 cm from the extrusion needle. The surface of the collector is covered with low-density polyethylene foil. The resulting fibres have a diameter of 250-600 nm and after being removed from the collector, they can be packed into 3D shapes (FIG. 8A and FIG. 8B).

Example 5: Hyaluronan Cotton Wool Prepared with a Extrusion Needle with 4 Capillaries The procedure was the same as in Example 2, only with the differences, that the extrusion needle had 4 capillaries of the length of 25.4 mm, having an internal diameter of 210 micrometers, and the blunt ends of the capillaries formed the vertices of a square of a side of 4.5 mm, the spinning solution was extruded at a rate of 0.18 mL/min per one capillary, the drying air was not directed by any cylinder and the surface of the collector was covered with polytetrafluoroethylene foil. The resulting fibres of diameter of 1-20 micrometers were removed from the collector in the form of thin layers that were packed into a bulky 3D structure (cotton wool).

Figure 9:
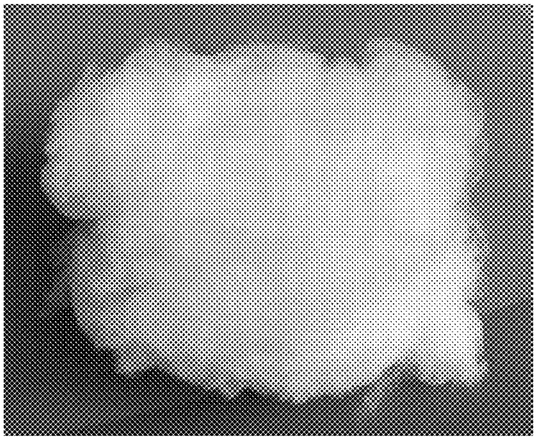
FIG. 9 shows 2 grams of cotton wool made of sodium hyaluronan prepared according to Example 6.

Example 6: Hyaluronan Cotton Wool Prepared on a Collector Formed by Bars 6 grams of sodium hyaluronan with the weight average molecular weight of 2.15 MDa are dispersed in 175.6 mL of 2-propanol. 168.2 mL of water is added to the resulting dispersion with thorough mixing, the solution is stirred for 24 hours at 20° C. until the polymer is completely dissolved, resulting in a 1.93% by weight solution of sodium hyaluronan. The spinning solution is then filled into a plastic syringe, which is inserted into a syringe pump. Subsequently, the spinning solution is spun on the device shown in FIG. 1. The spinning solution is extruded by a bent blunt extrusion needle of the length of 12.7 mm with an internal diameter of 160 micrometers with the rate of 0.4 mL/min. The extrusion needle is located coaxially under the point nozzle of the heat gun Wagner FURNO 750 so that the end of the extrusion needle is located 15 mm under the end of the point nozzle. The heat gun blows the drying air of temperature of 200° C. and absolute humidity of 11 g/$m^3$ with the volume flow of 280 L/min. The resulting fibres are carried by the air stream to the collector in the shape of a cylinder with a diameter of 15 cm formed by 38 bars with the thickness of 3 mm (shown in FIG. 5), rotating at the speed of 72 revolutions per minute and located 65 cm under the extrusion needle. The surface of the collector is covered with polytetrafluoroethylene foil. The resulting fibres having the diameter of 1-20 micrometers were removed from the collector in the form of thin layers that were packed into a bulky 3D structure (cotton wool) (FIG. 9).

Example 7: Hyaluronan Cotton Wool with the Molecular Weight of 0.83 MDa 2 grams of sodium hyaluronan having the weight average molecular weight of 0.83 MDa are dispersed in 31.6 mL of 2-propanol. 37.2 mL of water is added to the resulting dispersion with thorough mixing, the solution is stirred for 18 hours at 21° C. until the polymer is completely dissolved, resulting in a 3.14% by weight solution of sodium hyaluronan. The spinning solution is then filled into the cartridge of the pneumatic dispensing device, the cartridge is sealed and connected to the compressed air of +6 bar for 3 hours until the gas bubbles dissolve. Subsequently, the spinning solution is spun on the device shown in FIG. 2. The spinning solution is extruded by a blunt extrusion needle of the length of 6.4 mm with an internal diameter of 160 micrometers with the rate of 0.5 mL/min. The extrusion needle is located coaxially in the center of the air nozzle, the end of the needle is located 20 mm under the end of the air nozzle. The drying air flows from the air nozzle through an annular outlet with an internal diameter of 19 mm and an external diameter of 25 mm, the temperature of the drying air is 95° C., the absolute humidity is 0.2 $g/m^3$ and it flows with the volume flow of 400 L/min. The drying air is directed by a cylinder located coaxially with the extrusion needle, this cylinder of the internal diameter of 3.7 cm and the length of 17.5 cm starts 1 mm under the end of the extrusion needle. The resulting fibres are carried by the air stream to the collector in the shape of a cylinder with a diameter of 15 cm, rotating at the speed of 1.8 revolutions per minute and located 74 cm under the extrusion needle. The surface of the collector is covered with polytetrafluoro-ethylene foil. The resulting fibres of the diameter of 1-15 micrometers were removed from the collector in the form of thin layers that were packed into a bulky 3D structure (cotton wool).

Figure 10:
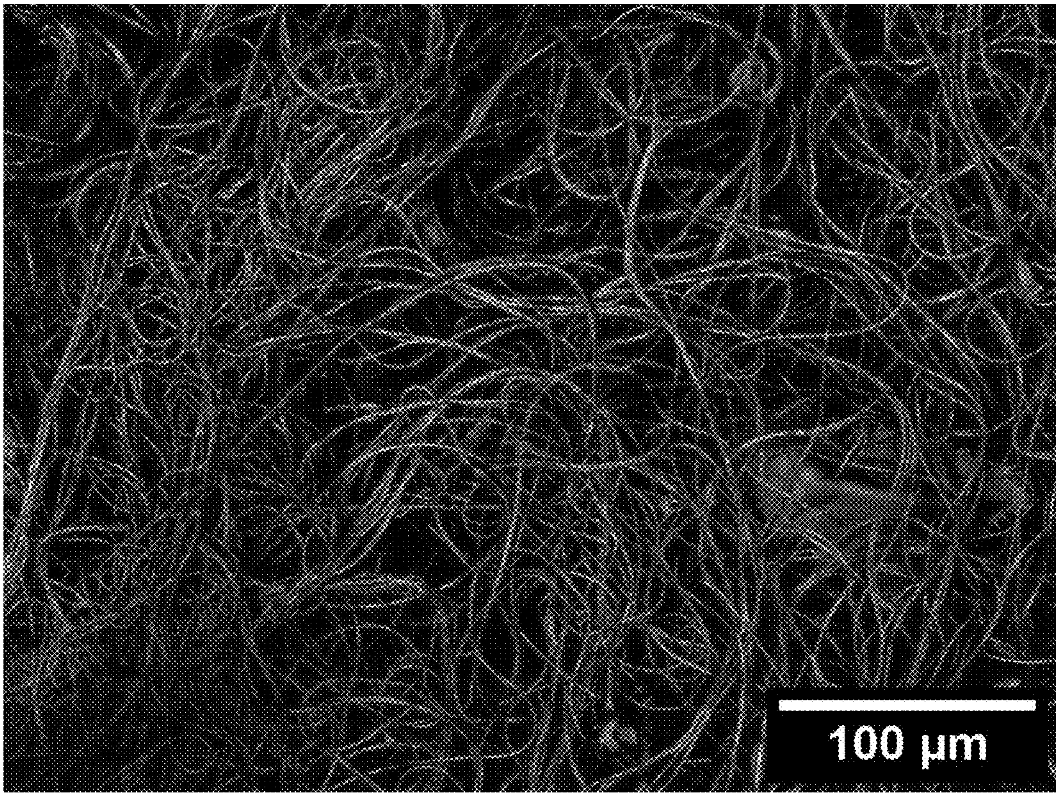
FIG. 10 shows the structure of the cotton wool made of sodium hyaluronan prepared according to Example 8.

Example 8: Hyaluronan Cotton Wool Prepared with the Needle of Size of 410 Micrometers The procedure was the same as in Example 3, only with the differences, that the extrusion needle had an internal diameter of 410 micrometers, the spinning solution was extruded at a rate of 0.86 mL/min, each heat gun blew the drying air of the temperature 250° C. and absolute humidity of 13 $g/m^3$ with the volume flow of 160 L/min and the surface of the collector was covered with low-density polyethylene foil. The resulting fibres have a diameter of 1-5 micrometers and were removed from the collector in the form of a thin layer that was packed into a bulky 3D structure (cotton wool) (FIG. 10).

Example 9: Hyaluronan Cotton Wool Prepared with the Drying Air of Temperature 600° C.

The procedure was the same as in the Example 3, only with the differences, that the spinning solution was extruded at a rate of 0.11 mL/min, each heat gun blew the drying air of the temperature of 600° C. and absolute humidity of 14 $g/m^3$ with the volume flow of 130 L/min and the surface of the collector was covered with low-density polyethylene foil. The resulting fibres have a diameter of 2-25 micrometers and were removed from the collector in the form of thin layer that was packed into a bulky 3D structure (cotton wool).

Example 10: Hyaluronan Nanofibres Prepared with a Needle of the Size of 80 Micrometers The procedure was the same as in the Example 4, only with the differences, that the extrusion needle had an internal diameter of 80 micrometers, the spinning solution was extruded at a rate of 0.0012 mL/min, the drying air was blown with the volume flow of 40 L/min and the collector was placed at the distance of 5 cm from the extrusion needle. The resulting fibres have the diameter of 150-600 nm.

Figure 11:
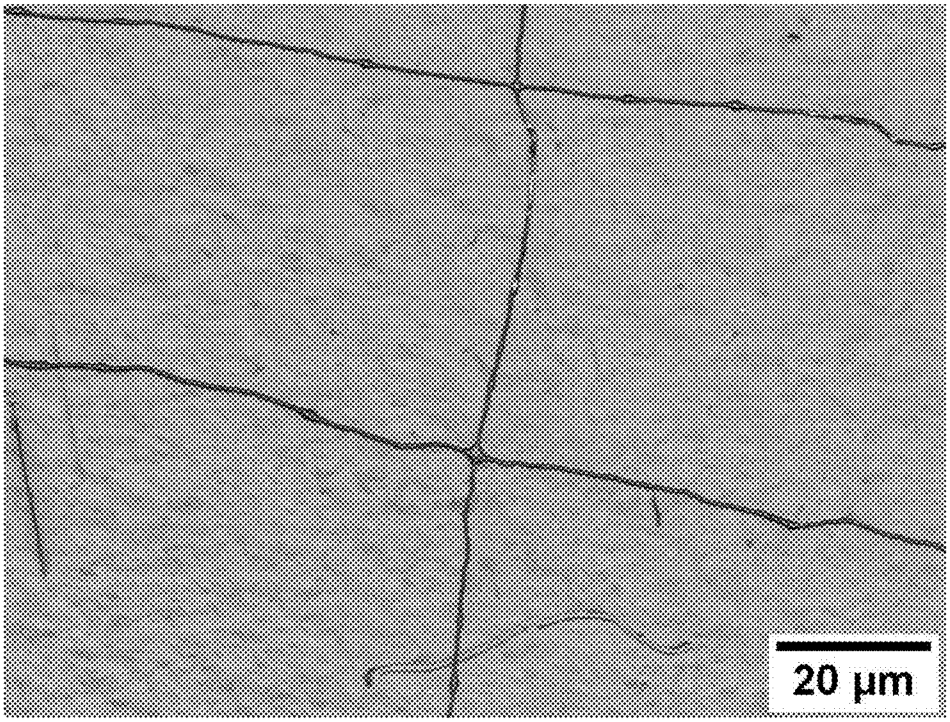
FIG. 11 shows nanofibres made of sodium hyaluronan on the surface of the collector prepared according to Example 11.

Example 11: Hyaluronan Nanofibres Prepared with the Drying Air Flow of 236 L/Min The procedure was the same as in Example 4, only with the differences, that the extrusion needle was sharpened to the tip, the spinning solution was extruded at a rate of 0.065 mL/min, the air nozzle blew the drying air with the volume flow of 236 L/min and the collector was placed at a distance of 20 cm from the extrusion needle. The resulting fibres (FIG. 11) have the diameter of 300-800 nm.

Figure 12:
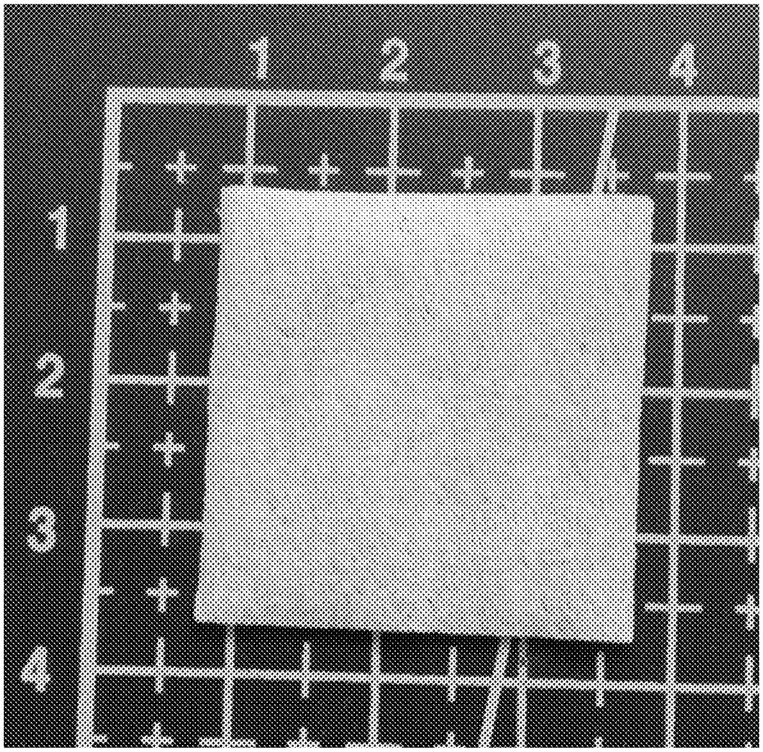
FIG. 12 shows a non-woven fabric made of sodium hyaluronan prepared according to Example 12.

Example 12: Non-Woven Fabric Made of Hyaluronan with the Area Weight of 103 $g/m^2$ 6 grams of sodium hyaluronan with the weight average molecular weight of 2.04 MDa are dispersed in 175.6 mL of 2-propanol. 168.2 mL of water is added to the resulting dispersion with thorough mixing, the solution is stirred for 7 hours at 20° C. until the polymer is completely dissolved, resulting in a 1.93% by weight solution of sodium hyaluronan. The spinning solution is then filled into the cartridge of the pneumatic dispensing device, the cartridge is sealed and connected to the compressed air of +6.8 bar for 5 hours until the gas bubbles dissolve. Subsequently, the spinning solution is spun on the device shown in FIG. 1 only with the difference, that the fibres are, after passing through the cylinder, carried in front of the second heat gun, which blows the drying air perpendicular to the axis of the extrusion needle and carries the fibres to the collector located off the axis of the extrusion needle in the horizontal direction from the second heat gun. The spinning solution is extruded by a bent blunt extrusion needle of the length of 12.7 mm with an internal diameter of 160 micrometers with the rate of 0.6 mL/min. The extrusion needle is located coaxially under the point nozzle of the upper heat gun Wagner FURNO 750 so that the end of the extrusion needle is located 15 mm under the end of the point nozzle. The upper heat gun blows the drying air of the temperature of 180° C. and absolute humidity of 7 $g/m^3$ with the volume flow of 280 L/min. The drying air is directed by a cylinder located coaxially with the extrusion needle, this cylinder of the internal diameter of 2.7 cm and the length of 21.5 cm starts at 1 mm under the end of the extrusion needle. The resulting fibres are carried by the air stream to the front of the lower heat gun Wagner FURNO 750, positioned so that its point nozzles orifice is 115 cm under the extrusion needle and 6 cm horizontally from the axis of the extrusion needle. The lower heat gun blows the drying air of the temperature of 120° C. and absolute humidity of 7 $g/m^3$ with the volume flow of 250 L/min. The resulting fibres are carried horizontally to the collector in the shape of a cylinder with a diameter of 15 cm rotating at the speed of 2 revolutions per minute, the center of which is located 122.5 cm under the extrusion needle and 15 cm from the axis of the extrusion needle. The surface of the collector is covered with polytetrafluoroethylene foil. The resulting non-woven fabric has the area weight of 103 $g/m^2$ and is made of fibres with the diameter of 1-20 micrometers (FIG. 12).

Example 13: Cotton Wool of Hyaluronan Prepared with Use of Ethanol as Organic Solvent 2 grams of sodium hyaluronan having the weight average molecular weight of 2 MDa are dispersed in 104.5 mL of ethanol. 67.0 mL of water is added to the resulting dispersion with thorough mixing, the solution is stirred for 20 hours at 24° C. until the polymer is completely dissolved, resulting in a 1.33% by weight solution of sodium hyaluronan. The spinning solution is then filled into the cartridge of the pneumatic dispensing device, the cartridge is sealed and connected to the compressed air of +6 bar for 2 hours until the gas bubbles dissolve. Subsequently, the spinning solution is spun on the device shown in FIG. 2. The spinning solution is extruded by a blunt extrusion needle of the length of 6.4 mm with an internal diameter of 160 micrometers with the rate of 0.51 mL/min. The extrusion needle is located coaxially in the center of the air nozzle, the end of the needle is located 20 mm under the end of the air nozzle. The drying air flows from the air nozzle through an annular outlet with an internal diameter of 19 mm and an external diameter of 25 mm, the temperature of the drying air is 106° C., the absolute humidity is 0.2 g/$m^3$ and it flows with the volume flow of 250 L/min. The drying air was not directed by any cylinder. The resulting fibres are carried by the air stream to the collector in the shape of a cylinder with a diameter of 15 cm, rotating at the speed of 2.4 revolutions per minute, located 74 cm under the extrusion needle. The surface of the collector is covered with polytetrafluoroethylene foil. The resulting fibres having the diameter of 1-15 micrometers were removed from the collector in the form of thin layers that were packed into a bulky 3D structure (cotton wool).

Example 14: Cotton Wool Made of Hyaluronan Prepared Using Acetone as the Organic Solvent The procedure was the same as in Example 2, only with the differences, that acetone was used instead of 2-propanol and 1.91% by weight of spinning sodium hyaluronan solution was prepared from 2 grams of sodium hyaluronan, 52.7 mL of acetone and 69.1 mL of water, the solution was extruded at a rate of 0.3 mL/min, the drying air was not directed by any cylinder, the collector was rotating at the speed of 1.8 revolutions per minute and its surface was covered with polytetrafluoroethylene foil. The resulting fibres having the diameter of 1-20 micrometers were removed from the collector in the form of thin layers that were packed into a bulky 3D structure (cotton wool).

Example 15: Cotton Wool Made of Hyaluronan Chloramide Having the Molecular Weight of 0.1 MDa 3 grams of hyaluronan chloramide having the weight average molecular weight of 0.1 MDa and substitution degree of 96% and 1 gram of sodium hyaluronan having the weight average molecular weight of 2 MDa are dispersed together in 52.7 mL of 2-propanol. 61.9 mL of water is added to the resulting dispersion with thorough mixing, the solution is stirred for 24 hours at 20° C. until the polymer is completely dissolved, resulting in a 3.74% by weight solution of the mixture of hyaluronan chloramide and sodium hyaluronan. The spinning solution is then filled into the cartridge of the pneumatic dispensing device, the cartridge is sealed and connected to the compressed air of +6.8 bar for 4 hours until the gas bubbles dissolve. Subsequently, the spinning solution is spun on the device shown in FIG. 1. The spinning solution is extruded by a bent blunt extrusion needle having the length of 12.7 mm with an internal diameter of 160 micrometers with the rate of 0.55 mL/min. The extrusion needle is located coaxially under the point nozzle of the heat gun Wagner FURNO 750 so that the end of the extrusion needle is located 15 mm under the end of the point nozzle. A heat gun blows the drying air of the temperature of 160° C. and absolute humidity of 8 g/$m^3$ with the volume flow of 280 L/min. The resulting fibres are carried by the air stream to the collector in the shape of a cylinder with a diameter of 15 cm, rotating at the speed of 2 revolutions per minute and located 115 cm under the extrusion needle. The surface of the collector is covered with polytetrafluoroethylene foil. The resulting fibres of the diameter of 2-50 micrometers were removed from the collector in the form of thin layers that were packed into a bulky 3D structure (cotton wool).

Basically the same result differing only in the ratio of chloramide hyaluronan and sodium hyaluronan can be achieved by the same procedure, with the only differences:

a) a 2.83% by weight spinning solution of a mixture of hyaluronan chloramide and sodium hyaluronan is prepared from 2 grams of hyaluronan chloramide, 1 gram of sodium hyaluronan, 52.7 mL of 2-propanol and 61.9 mL of water, this solution is extruded by the extrusion needle with the rate of 0.4 mL/min and the temperature of the drying air is 180° C.

b) a 2.90% by weight spinning solution of a mixture of hyaluronan chloramide and sodium hyaluronan is prepared from 2 grams of hyaluronan chloramide, 2 grams of sodium hyaluronan, 60.0 mL of 2-propanol and 87.3 mL of water, this solution is extruded by the extrusion needle with the rate of 0.47 mL/min and the temperature of the drying air is 180° C.

c) a 2.93% by weight spinning solution of a mixture of hyaluronan chloramide and sodium hyaluronan is prepared from 2 grams of hyaluronan chloramide, 2 grams of sodium hyaluronan, 67.8 mL of 2-propanol and 79.6 mL of water, this solution is extruded by the extrusion needle with the rate of 0.47 mL/min and the temperature of the drying air is 160° C.

Example 16: Cotton Wool from Hyaluronan Chloramide with the Molecular Weight of 0.39 MDa 2 grams of hyaluronan chloramide with the weight average molecular weight of 0.39 MDa and the substitution degree of 85% and 1 gram of sodium hyaluronan with the weight average molecular weight of 2.15 MDa are dispersed together in 58.5 mL of 2-propanol. 56.1 mL of water is added to the resulting dispersion with thorough mixing, the solution is stirred for 23 hours at 22° C. until the polymer is completely dissolved, resulting in the solution of the mixture of 2.87% by weight of hyaluronan chloramide and sodium hyaluronan. The spinning solution is then filled into a plastic syringe, which is inserted into the syringe pump. Subsequently, the spinning solution is spun on the device shown in FIG. 1. The spinning solution is extruded by a bent blunt extrusion needle of the length of 12.7 mm, having the internal diameter of 160 micrometers, with the rate of 0.4 mL/min. The extrusion needle is located coaxially under the point nozzle of the heat gun Wagner FURNO 750 so that the end of the extrusion needle is located 15 mm under the end of the point nozzle. The heat gun blows the drying air of 200° C. and absolute humidity of 7 g/$m^3$ with the volume flow 280 L/min. The resulting fibres are carried by the air stream on the collector in the form of a plate covered with polytetrafluoroethylene foil, which is located 140 cm under the end of the extrusion needle. The resulting fibres having the diameter of 1-90 micrometers were removed from the collector in the form of thin layers that were packed into a bulky 3D structure (cotton wool).

Figure 13:
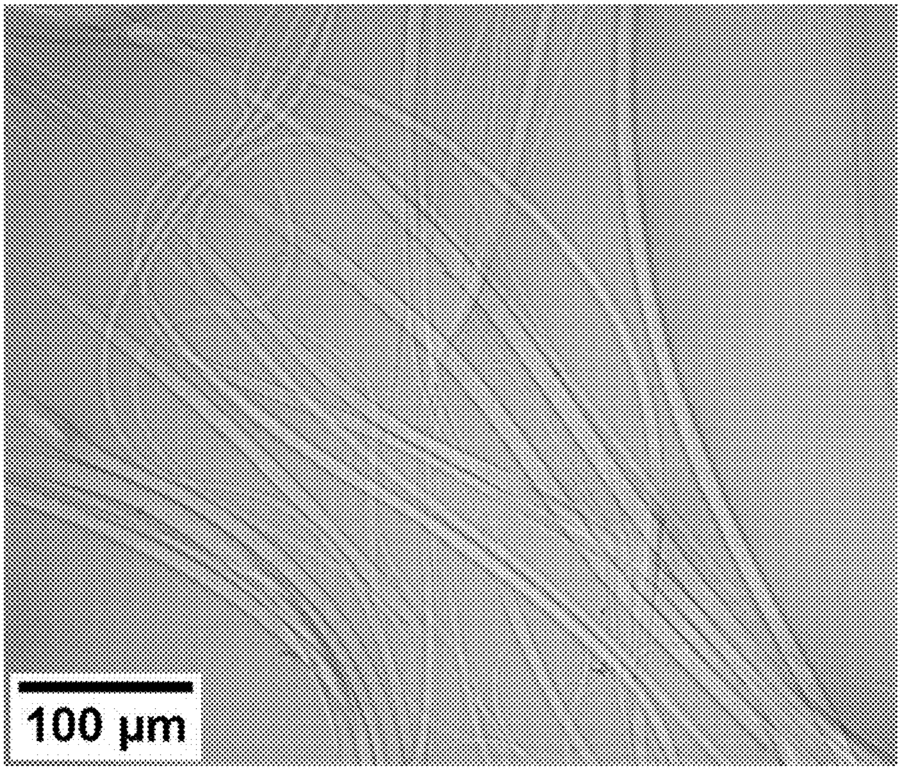
FIG. 13 shows fibres from the mixture of sodium hyaluronan and hyaluronan 3-(2-furanyl)acryloyl ester prepared according to Example 17 after 3 weeks in phosphate buffer.

Example 17: Non-Woven Fabric from Hyaluronan 3-(2-Furanyl)Acryloyl Ester and its Crosslinking 2 grams of sodium hyaluronan with the weight average molecular weight of 2 MDa and 2 grams of hyaluronan 3-(2-furanyl)acryloyl ester with the weight average molecular weight of 98 kDa and the substitution degree of 12.5% are dispersed in 95.8 mL of 2-propanol. 91.7 mL of water is added to the resulting dispersion with thorough mixing, the solution is stirred until the hyaluronan is completely dissolved for 8 hours at 25° C., resulting in a solution of the mixture of 2.3% by weight of hyaluronan chloramide and hyaluronan 3-(2-furanyl)acryloyl ester. The spinning solution is then filled into the cartridge of the pneumatic dispensing device, the cartridge is sealed and connected to the compressed air of +6 bar for 3 hours until the gas bubbles dissolve. Subsequently, the spinning solution is spun on the device shown in FIG. 3. The spinning solution is extruded by a blunt extrusion needle of the length of 12.7 mm with the internal diameter of 160 micrometers with the rate of 0.2 mL/min. The extrusion needle is located coaxially in the Luer Lock outlet of a common pneumatic dispenser cartridge having the volume of 55 mL, the end of the needle is located 1 mm under the end of the outlet from the cartridge. Through this outlet the air flows, having the temperature of 22° C. and absolute humidity of 0.2 $g/m^3$, with the volume flow of 36 L/min. This air carries the stream of the spinning solution through a gap having the width of 9 mm between two metal sheets forming an angle with each other 90°, the gap between the plates being located 7 mm under the end of the extrusion needle. A heat gun Wagner FURNO 750 is placed under each sheet, the gun having a wide nozzle so that the distance between the ends of the nozzles of both guns is 6 cm. Each gun blows the drying air of 350° C. and absolute humidity of 13 $g/m^3$ with the volume flow of 280 L/min. The resulting fibres are carried by the air stream onto the collector which is in the form of a plate covered with polytetrafluoroethylene foil and is located 40 cm under the end of the extrusion needle. The resulting non-woven fabric has the area weight of 11.6 $g/m^2$ and is made of fibres with the diameter of 3-10 micrometers. Crosslinking of hyaluronan 3-(2-furanyl)acryloyl ester contained in the fabric was done in the device Ultraviolet crosslinker CL-1000 (Fisher Scientific), where the fabric was exposed to radiation of wavelength 302 nm and energy intensity of 350 $\mu J/cm^2$ for 60 minutes. To verify insolubility, a sample of the fabric was placed in phosphate buffer at the temperature of 20° C., after 3 weeks the fibrous structure was retained (FIG. 13).

Example 18: Cotton Wool from Lauroyl Hyaluronan Having the Molecular Weight of 0.1 MDa 4 grams of lauroyl hyaluronan with the weight average molecular weight of 0.1 MDa and containing 18.3% by weight of the bound lauric acid are dispersed in 42.0 mL of 2-propanol. 61.1 mL of water is added to the resulting dispersion with thorough mixing, the solution is stirred for 4 hours at 25° C. until the polymer is completely dissolved, resulting in a 4.09% by weight solution of lauroyl hyaluronan. The spinning solution is then filled into the cartridge of the pneumatic dispensing device, the cartridge is sealed and connected to the compressed air of +5 bar for 2 hours until the gas bubbles dissolve. Subsequently, the spinning solution is spun on the device shown in FIG. 2. The spinning solution is extruded by conical polypropylene extrusion needle with an internal diameter of extrusion opening 160 micrometers with the rate of 1.6 mL/min. The extrusion needle is located coaxially in the center of the air nozzle, the end of the needle is located 26 mm under the end of the air nozzle. The drying air flows from the air nozzle through an annular outlet with an internal diameter of 19 mm and an external diameter of 25 mm, the temperature of the drying air is 73° C., the absolute humidity is 0.2 $g/m^3$ and it flows with the volume flow 250 L/min. The resulting fibres are carried by the air stream to the collector having the shape of a cylinder with a diameter of 15 cm and rotating at speed 1.8 revolutions per minute, which is located 73 cm under the extrusion needle. The collector surface is covered with polyester non-reinforced knitted fabric Zuzana (manufacturer: SILK & PROGRESS). The resulting fibres having the diameter of 10-90 micrometers were removed from the collector in the form of thin layers that were packed into a bulky 3D structure (cotton wool).

Figure 14:
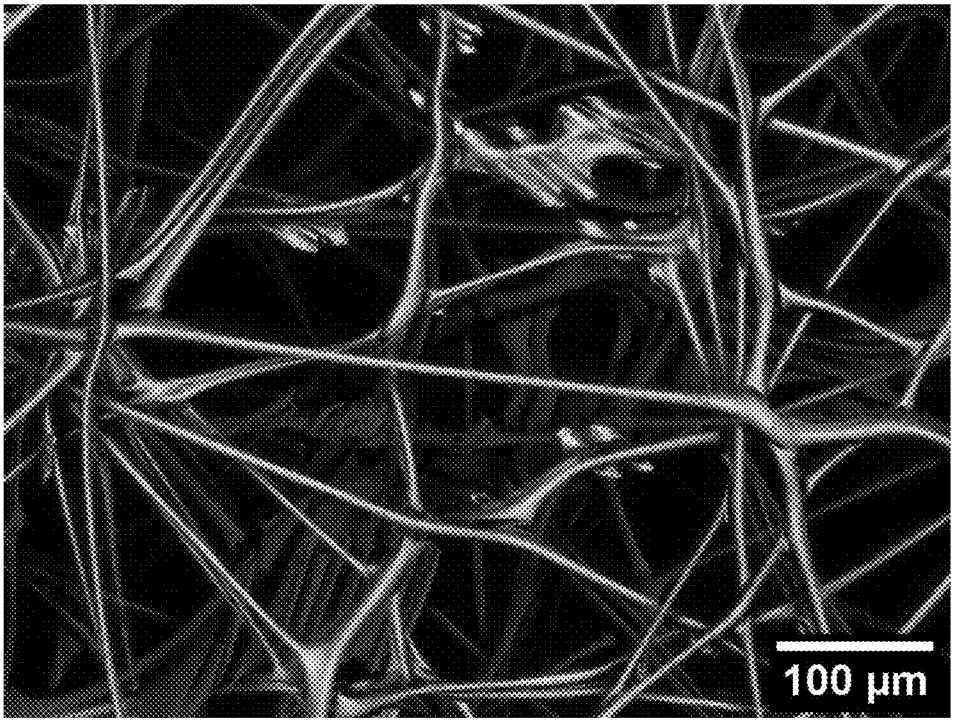
FIG. 14 shows the structure of cotton wool made of lauroyl hyaluronan prepared according to Example 19, in the upper part of the picture it can be clearly seen where the fibres were in contact with the knitted fabric covering the collector.

Example 19: Cotton Wool from Lauroyl Hyaluronan Having the Molecular Weight of 0.33 MDa 4 grams of lauroyl hyaluronan with the weight average molecular weight of 0.33 MDa and containing 16.8% by weight of the bound lauric acid are dispersed in 42.0 mL of 2-propanol. 61.1 mL of water is added to the resulting dispersion with thorough mixing, the solution is stirred until the polymer is completely dissolved for 4 hours at 23° C., resulting in a 4.09% by weight solution of lauroyl hyaluronan. The spinning solution is then filled into the cartridge of the pneumatic dispensing device, the cartridge is sealed and connected to the compressed air of +5 bar for 1 hour until the gas bubbles dissolve. Subsequently, the spinning solution is spun on the device shown in FIG. 2. The spinning solution is extruded by a blunt extrusion needle of the length of 6.4 mm with an internal diameter of 160 micrometers with the rate of 0.4 mL/min. The extrusion needle is located coaxially in the center of the air nozzle, the end of the needle is located 20 mm under the end of the air nozzle. The drying air flows from the air nozzle through an annular outlet with an internal diameter of 19 mm and an external diameter of 25 mm, the temperature of the drying air is 52° C., the absolute humidity is 0.2 $g/m^3$ and it flows with the volume flow of 100 L/min. The resulting fibres are carried by the air stream to the collector having the shape of a cylinder with a diameter of 15 cm rotating at the speed of 2 revolutions per minute, which is located 40 cm under the extrusion needle. The collector surface is covered with polyester non-reinforced knitted fabric Zuzana (manufacturer: SILK & PROGRESS). The resulting fibres having the diameter of 5-20 micrometers were removed from the collector in the form of thin layers that were packed into a bulky 3D structure (cotton wool) (FIG. 14).

Figure 15:
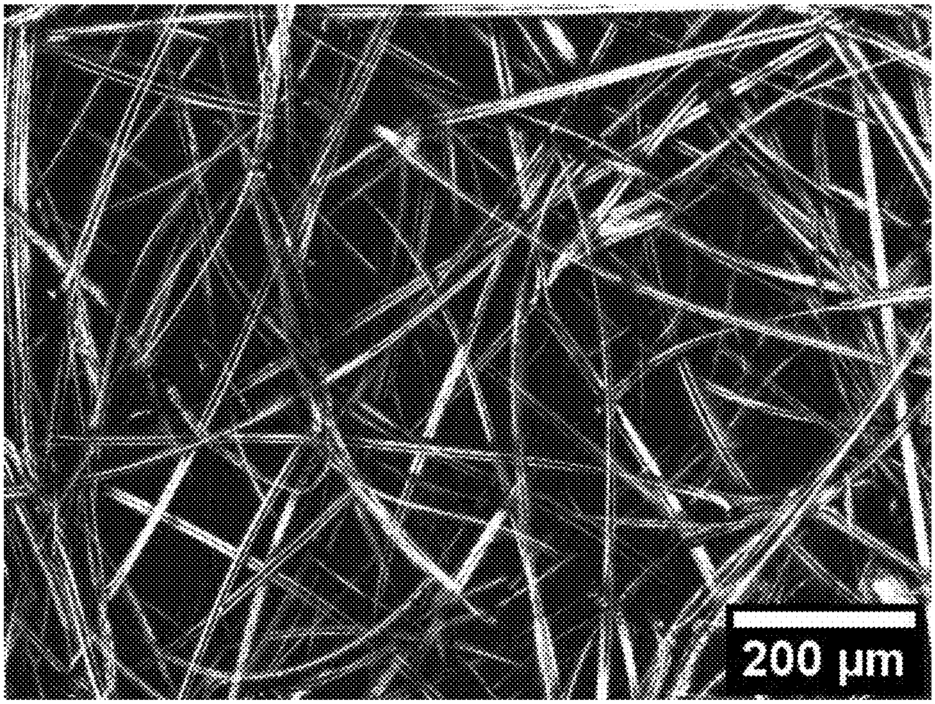
FIG. 15 shows the structure of cotton wool made of lauroyl hyaluronan prepared according to Example 20.

Example 20: Cotton Wool from Lauroyl Hyaluronan with the Molecular Weight of 1 MDa 2 grams of lauroyl hyaluronan having the weight average molecular weight of 1 MDa and containing 16% by weight of the bound lauric acid are dispersed in 47.9 mL of 2-propanol. 45.9 mL of water is added to the resulting dispersion with thorough mixing, the solution is stirred until the polymer is completely dissolved for 6 hours at 20° C., resulting in a 2.35% by weight solution of lauroyl hyaluronan. The spinning solution is then filled into a plastic syringe, which is inserted into the syringe pump. Subsequently, the spinning solution is spun on the device shown in FIG. 1. The spinning solution is extruded by a bent blunt extrusion needle of the length of 12.7 mm with an internal diameter of 160 micrometers with the rate of 0.4 mL/min. The extrusion needle is located coaxially under the point nozzle of the heat gun Wagner FURNO 750 so that the end of the extrusion needle is located 15 mm under the end of the point nozzle. The heat gun blows the drying air of the temperature of 200° C. and absolute humidity of 7 $g/m^3$ with the volume flow of 130 L/min. The resulting fibres are carried by the air stream to the collector in the shape of a cylinder with a diameter of 15 cm formed by 38 bars with the thickness of 3 mm (shown in FIG. 5) rotating at the speed of 72 revolutions per minute and located 65 cm under the extrusion needle. The surface of the collector is covered with polytetrafluoroethylene foil. The resulting fibres having the diameter of 5-50 micrometers were removed from the collector in the form of thin layers that were packed into a bulky 3D structure (cotton wool) (FIG. 15).

Example 21: Cotton Wool from a Mixture of Hyaluronan and Carboxymethyl Cellulose 2 grams of sodium hyaluronan with the weight average molecular weight of 2 MDa and 1 gram of sodium carboxymethyl cellulose with the weight average molecular weight of 90 kDa are dispersed in 52.7 mL of 2-propanol. 61.9 mL of water is added to the resulting dispersion with thorough mixing, the solution is stirred for 20 hours at 21° C. until the hyaluronan is completely dissolved, resulting in a solution of a mixture of 2.83% by weight of sodium hyaluronan and sodium carboxymethyl cellulose. The spinning solution is then filled into the cartridge of the pneumatic dispensing device, the cartridge is sealed and connected to the compressed air of +6.8 bar for 4 hours until the gas bubbles dissolve. Subsequently, the spinning solution is spun on the device shown in FIG. 2. The spinning solution is extruded by a blunt extrusion needle having the length of 6.4 mm and an internal diameter of 160 micrometers with the rate of 0.5 mL/min. The extrusion needle is located coaxially in the center of the air nozzle, the end of the needle is located 20 mm under the end of the air nozzle. The drying air flows from the air nozzle through an annular outlet with an internal diameter of 19 mm and an external diameter of 25 mm, the temperature of the drying air is 106° C., the absolute humidity is 0.2 $g/m^3$ and it flows with the volume flow of 250 L/min. The drying air is directed by a cylinder located coaxially with the extrusion needle, said cylinder having the internal diameter of 3.7 cm and the length of 17.5 cm starts 1 mm under the end of the extrusion needle. The resulting fibres are carried by the air stream to the collector in the shape of a cylinder with a diameter of 15 cm, rotating at the speed of 1.8 revolutions per minute and located 74 cm under the extrusion needle. The surface of the collector is covered with a polytetrafluoroethylene foil. The resulting fibres having the diameter of 2-40 micrometers were removed from the collector in the form of thin layers that were packed into a bulky 3D structure (cotton wool).

Figure 16:
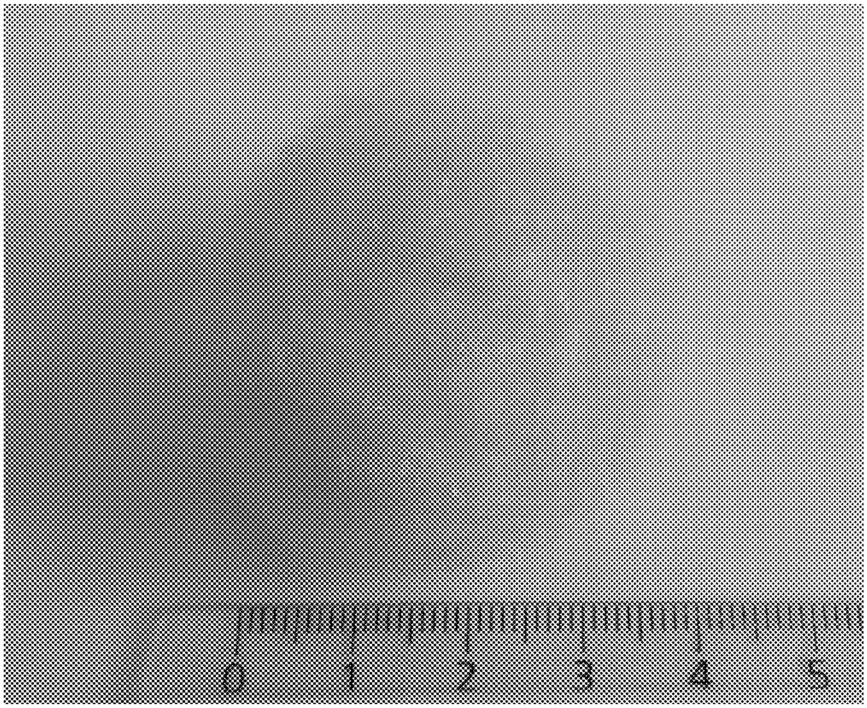
FIG. 16 shows cotton wool from the mixture of sodium hyaluronan and oxycellulose prepared according to Example 22.

Example 22: Cotton Wool from a Mixture of Hyaluronan and Oxycellulose 2 grams of sodium hyaluronan with the weight average molecular weight of 2.13 MDa and 2.35 grams of oxycellulose (Okcel Na-M, Synthesia a.s., Czech Republic) are dispersed in 42.9 mL of 2-propanol. 78.3 mL of water is added to the resulting dispersion with thorough mixing, the solution is stirred for 22 hours at 21° C. until the hyaluronan is completely dissolved, resulting in a 1.73% by weight solution of sodium hyaluronan with dispersed 2.03% by weight of oxycellulose. The spinning solution is then filled into the cartridge of the pneumatic dispensing device, the cartridge is sealed and connected to the compressed air of +6 bar for 3 hours until the gas bubbles dissolve. Subsequently, the spinning solution is spun on the device shown in FIG. 1. The spinning solution is extruded by a bent blunt extrusion needle of the length of 12.7 mm having an internal diameter of 210 micrometers, with the rate 0.54 mL/min. The extrusion needle is located coaxially under the point nozzle of the heat gun Wagner FURNO 750 so that the end of the extrusion needle is located 15 mm under the end of the point nozzle. The heat gun blows the drying air having the temperature of 100° C. and absolute humidity of 7 $g/m^3$ with the volume flow of 230 L/min. The drying air is directed by a cylinder located coaxially with the extrusion needle, said cylinder having the internal diameter of 2.7 cm and the length of 21.5 cm starts 1 mm under the end of the extrusion needle. The resulting fibres are carried by the air stream to the collector in the shape of a cylinder with a diameter of 15 cm, rotating at the speed of 2 revolutions per minute and located 115 cm under the extrusion needle. The surface of the collector is covered with a polytetrafluoroethylene foil. The resulting fibres of the diameter of 40-100 micrometers were removed from the collector in the form of thin layers that were packed into a bulky 3D structure (cotton wool) (FIG. 16).

Example 23: Cotton Wool from Hyaluronan Containing Octenidine Dihydrochloride 4.5 grams of sodium hyaluronan having the weight average molecular weight of 1.5 MDa are dispersed in 131.0 mL of 2-propanol. First 9 mg of octenidine dihydrochloride dissolved in 0.7 mL of ethanol and then 126.1 mL of water are added to the resulting dispersion with thorough mixing, the solution is stirred until the polymer is completely dissolved for 7 hours at 21° C., resulting in a 1.93% by weight solution of sodium hyaluronan containing 0.2% by weight octenidine dihydrochloride in dry matter. The spinning solution is then filled into the cartridge of the pneumatic dispensing device, the cartridge is sealed and connected to the compressed air of +6.8 bar for 2 hours until the gas bubbles dissolve. Subsequently, the spinning solution is spun on the device shown in FIG. 1. The spinning solution is extruded by a bent blunt extrusion needle having the length of 12.7 mm and an internal diameter of 160 micrometers with the rate of 0.5 mL/min. The extrusion needle is located coaxially under the point nozzle of the heat gun Wagner FURNO 750 so that the end of the extrusion needle is located 15 mm under the end of the point nozzle. The heat gun blows the drying air of the temperature of 180° C. and absolute humidity of 11 $g/m^3$ with the volume flow 280 L/min. The drying air is directed by a cylinder located coaxially with the extrusion needle, said cylinder having the internal diameter of 2.7 cm and the length of 21.5 cm starts 1 mm under the end of the extrusion needle. The resulting fibres are carried by the air stream to the collector in the shape of a cylinder with a diameter of 15 cm formed by 38 bars with the thickness of 3 mm (shown in FIG. 5) rotating at the speed of 2 revolutions per minute and located 115 cm under the extrusion needle. The surface of the collector is covered with a polytetrafluoroethylene foil. The resulting fibres having the diameter of 1-20 micrometers and containing 0.2% by weight of octenidine dihydrochloride were removed from the collector in the form of thin layers that were packed into a bulky 3D structure (cotton wool).

Figure 17:
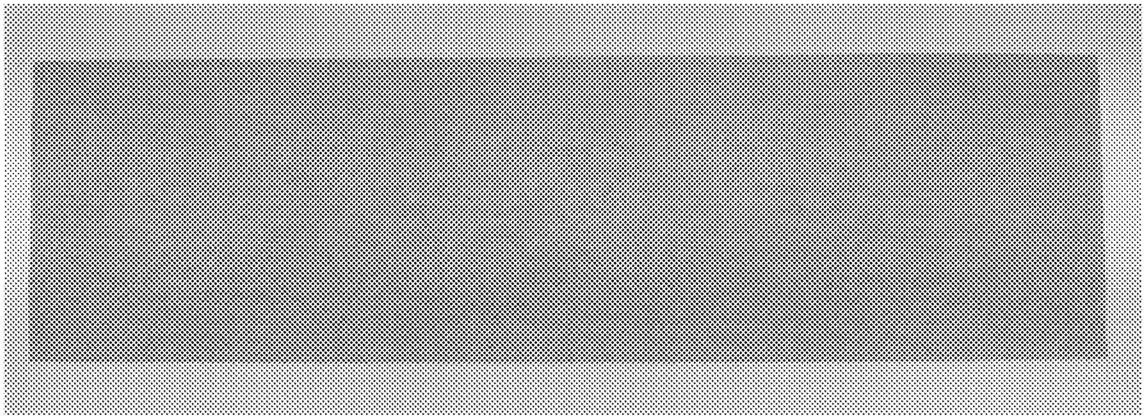
FIG. 17 shows a non-woven fabric made of sodium hyaluronan containing blue dye Patent Blue VF prepared according to Example 24 illuminated by the lower light.

Example 24: Non-Woven Fabric from Hyaluronan Containing the Dye Patent Blue VF 4 grams of sodium hyaluronan having the weight average molecular weight of 2.13 MDa and 36 mg of the dye Patent Blue VF are dispersed in 117.0 mL of 2-propanol. 112.0 mL of water is added to the resulting dispersion with thorough mixing, the solution is stirred for 21 hours at 20° C. until the polymer is completely dissolved, resulting in a 1.93% by weight solution of sodium hyaluronan containing 0.8% by weight of the dye Patent Blue VF in dry matter. The spinning solution is then filled into the cartridge of the pneumatic dispensing device, the cartridge is sealed and connected to the compressed air of +6.8 bar for 6 hours until the gas bubbles dissolve. Subsequently, the spinning solution is spun on the device shown in FIG. 1. The spinning solution is extruded by a bent blunt extrusion needle having the length of 12.7 mm and an internal diameter of 160 micrometers with the rate of 0.4 mL/min. The extrusion needle is located coaxially under the point nozzle of the heat gun Wagner FURNO 750 so that the end of the extrusion needle is located 15 mm under the end of the point nozzle. The heat gun blows the drying air of the temperature of 190° C. and absolute humidity of 5 g/$m^3$ with the volume flow of 280 L/min. The drying air is directed by a cylinder located coaxially with the extrusion needle, said cylinder having the internal diameter of 2.7 cm and the length of 21.5 cm starts 1 mm under the end of the extrusion needle. The resulting fibres are carried by the air stream to the collector in the shape of a cylinder with a diameter of 15 cm, rotating at the speed of 2 revolutions per minute and located 115 cm under the extrusion needle. The surface of the collector is covered with a polytetrafluoroethylene foil. The resulting non-woven fabric of blue color has the area weight of 11.0 g/$m^2$ and is made of fibres having the diameter of 1-20 micrometers (FIG. 17).

Figure 18:
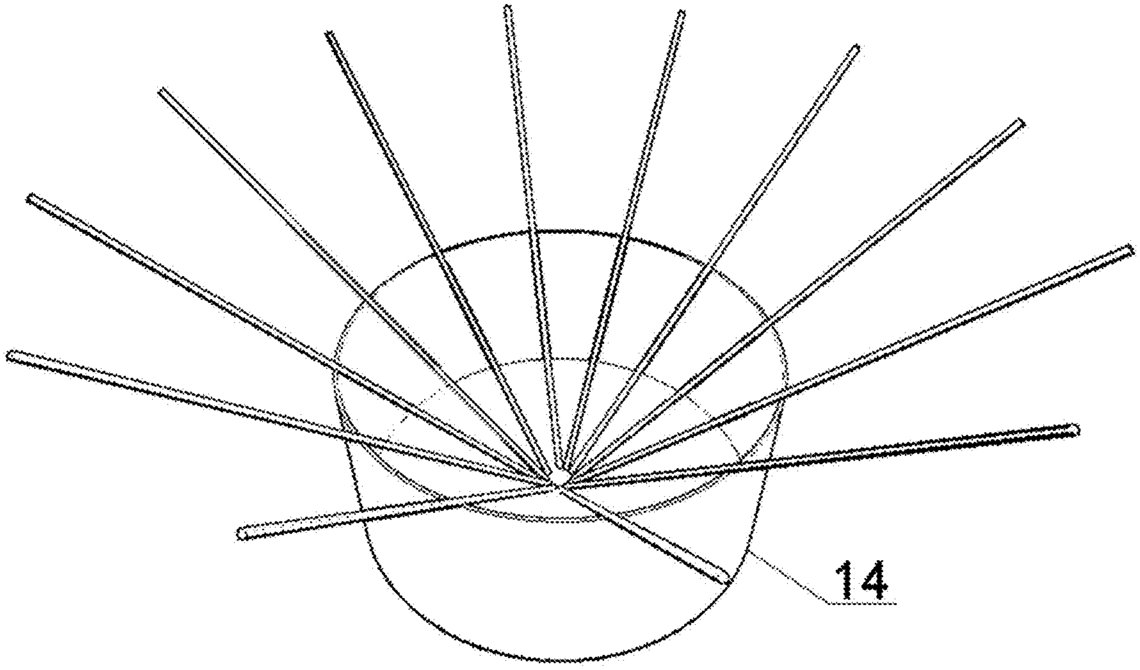
FIG. 18 shows stationary collector formed by bars.
Figure 19:
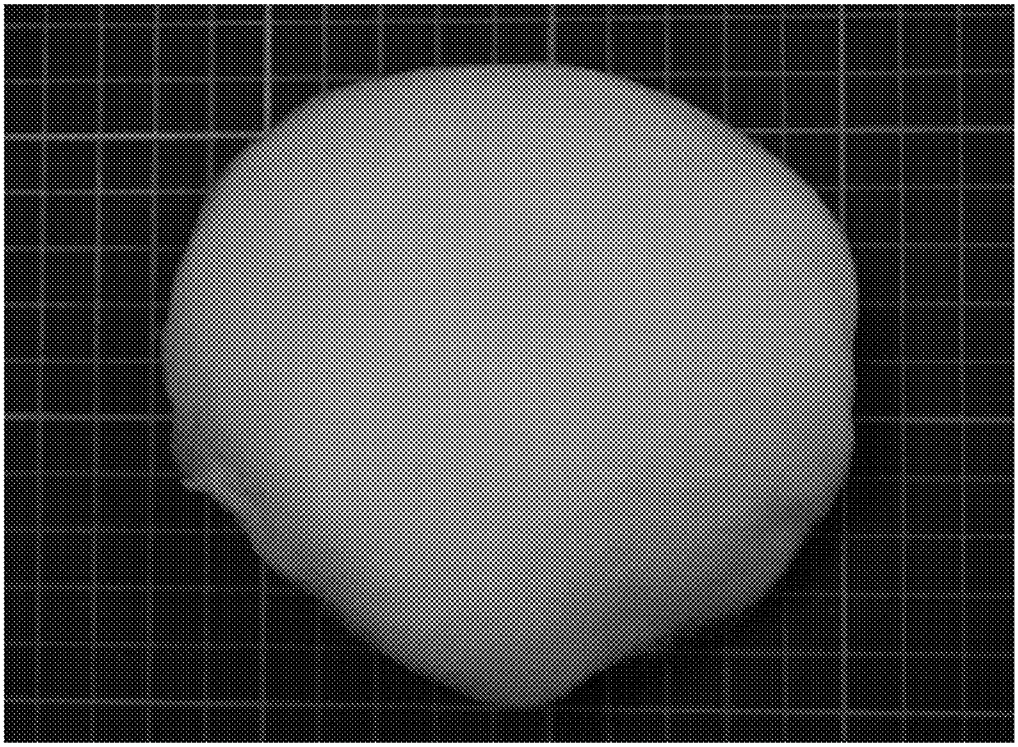
FIG. 19 shows a sample of cotton wool having the weight of 1.6 g and made of sodium hyaluronan prepared according to Example 25.

Example 25: Bulky Hyaluronan Cotton Wool Prepared on a Stationary Collector 4 grams of sodium hyaluronan having the weight average molecular weight of 2.04 MDa are dispersed in 117.1 mL of 2-propanol. 112.1 mL of water is added to the resulting dispersion with thorough mixing, the solution is stirred for 22 hours at 20° C. until the polymer is completely dissolved resulting in a 1.93% by weight solution of sodium hyaluronan. The spinning solution is then filled into the cartridge of the pneumatic dispensing device, the cartridge is sealed and connected to the compressed air of +6.5 bar for 4 hours until the gas bubbles dissolve. Subsequently, the spinning solution is spun on the device shown in FIG. 2. The spinning solution is extruded by a blunt extrusion needle having the length of 6.4 mm and an internal diameter of 160 micrometers with the rate of 0.24 mL/min. The extrusion needle is located coaxially in the center of the air nozzle, the end of the needle is located 20 mm under the end of the air nozzle. The drying air flows from the air nozzle through an annular outlet with an internal diameter of 19 mm and an external diameter of 25 mm, the temperature of the drying air is 100° C., the absolute humidity is 0.2 g/$m^3$ and it flows with the volume flow of 400 L/min. The drying air is directed by a cylinder located coaxially with the extrusion needle, said cylinder having the internal diameter of 3.7 cm and the length of 17.5 cm starts 1 mm under the end of the extrusion needle. The resulting fibres are carried by the air stream to the stationary collector (shown in FIG. 18) having the shape of an inverted pyramid and located in a cylindrical container having the height of 12 cm and the internal diameter of 26 cm, the lateral edges of the pyramid are formed by 12 bars having the length of 34 cm and the thickness of 2 mm and the opposite lateral edges together form an angle of 90°. The bottom of the cylindrical container, which is a part of the collector, is located 112 cm under the extrusion needle. The surface of the collector is covered with a polytetrafluoroethylene foil. The resulting fibres having the diameter of 0.5-3 micrometers on the collector bars directly create a bulky 3D material (cotton wool) (FIG. 19).

Figure 20:
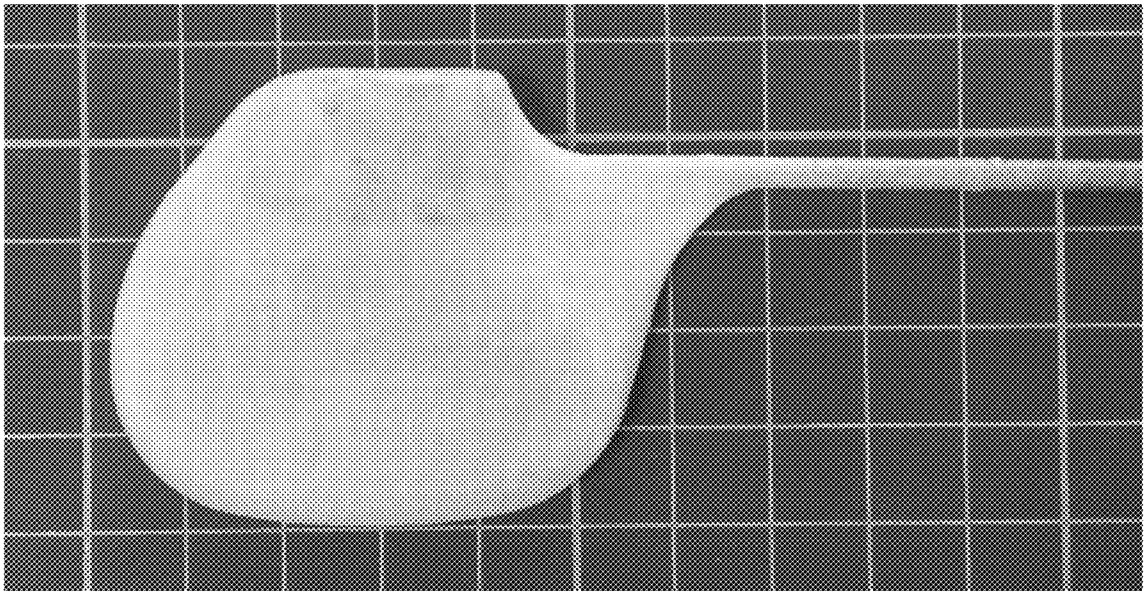
FIG. 20 shows a pacemaker covered with non-woven fabric made of sodium hyaluronan prepared according to Example 26.

Example 26: Non-Woven Fabric Made of Hyaluronan Deposited on the Surface of a Peacemaker The procedure was the same as in Example 25, only with the difference, that a pacemaker Biotronik Actros DR, mounted on the collector axis rotating at the speed of 13.5 revolutions per minute 65 cm under the extrusion needle, was used as a collector. The resulting non-woven fabric covering the pacemaker has the area weight of 12 g/$m^2$ and is made of fibres having the diameter of 0.5-3 micrometers (FIG. 20).

OVERVIEW OF REFERENCE SIGNS IN THE DRAWINGS

1 compressor
2 heating element
3 heat gun
4 outlet opening of the air nozzle
4*a*, 4*b* outlet openings of additional nozzles
5 air nozzle
5*a*, 5*b* additional air nozzles
6 outlet from the air nozzle
7 focusing panels (in perspective view)
8 dosing device
81 piston
9 solution
10 tube
11 extrusion part (e.g., needle)
11*a* dispensing opening
12 fibres
13 focusing part
14 collector

The invention claimed is:

1. A method of preparing fibres based on hyaluronic acid, a water-soluble metal compound thereof, and/or a derivative thereof by dry spinning, said method comprising:

preparing a spinning solution comprising from 1 to 5% by weight of hyaluronic acid and/or a water-soluble metal or non-metal salt thereof or a water-soluble mixture of metal and/or non-metal salts of hyaluronic acid and/or hyaluronic acid derivative, dissolved in from 28 to 54% by weight of organic solvent and from 44 to 70% by weight of water, each based on the total weight of the spinning solution; and extruding the spinning solution through at least one opening of an extrusion part into a drying air stream to give fibres that are carried to a collector, wherein the at least one opening has a diameter of from 80 to 410 μm, and wherein the spinning solution is extruded at a rate of from 0.001 to 1.6 mL/min to prepare the fibers.

2. The method of 1, wherein the spinning solution comprises: (i) a water-soluble metal or non-metal salt of hyaluronic acid selected from the group of Na+, K+, Li+, Ag+, Au+, and NH4+ salts of hyaluronic acid and combinations thereof; (ii) a hyaluronic acid derivative selected from the group of hyaluronan chloramide, hyaluronan 3-(2-furanyl) acryloyl ester, hyaluronan tyramine, hyaluronan benzyl ester, hyaluronan ethyl ester, and acylated derivatives of hyaluronan selected from the group of capronoyl, capryloyl, caprinoyl, lauroyl, myristoyl, palmitoyl, stearoyl, and oleoyl hyaluronan, and combinations thereof; or (iii) both (i) and (ii).

3. The method of claim 2, wherein the spinning solution comprises hyaluronan chloramide or a mixture of hyaluronan chloramide and native hyaluronic acid, and wherein the substitution degree of hyaluronan chloramide is from 0.1% to 100%.

4. The method of claim 1, wherein the organic solvent is: (i) selected from the group of methanol, tetrahydrofuran, methyl acetate, methyl ethylketone, 1,2-dimethoxyethane, acetonitrile, isopropylalcohol, 1-propanol, ethanol, acetone, and combinations there; (ii) is present in the spinning solution in an amount of from 40 to 45% by weight; or (iii) both (i) and (ii).

5. The method of claim 1, wherein the spinning solution is prepared by first dispersing the hyaluronic acid and/or the water-soluble metal or non-metal salt thereof or the water-soluble mixture of metal and/or non-metal salts of hyaluronic acid and/or the hyaluronic acid derivative in the organic solvent to give a dispersion, then adding the water to the dispersion with thorough mixing to begin preparing a solution, and then stirring the solution for 1 to 24 hours at a temperature of from 20 to 30° C. to achieve complete dissolution, thereby giving the spinning solution.

6. The method of claim 1, further comprising, before extrusion, disposing the prepared spinning solution into a cartridge, sealing the cartridge, and then exposing the spinning solution to compressed air at from +5 to +7 bar for a period of from 1 to 8 hours to dissolve all gas bubbles.

7. The method of claim 1, further comprising flowing a stream of cooled air around the extrusion part to carry the spinning solution into the drying air stream, where the drying air stream comprises warmed drying air.

8. The method of claim 1, wherein:

(i) the drying air comprises a temperature of from 15 to 600° C., an absolute humidity of from 0 to 14 g/$m^3$, and a flow rate of from 1.6 to 315 m/s;

(ii) the drying air is directed by one or more hollow cylinders; or (iii) both (i) and (ii).

9. The method of claim 1, wherein the fibres are deposited on the collector, and wherein the collector is: (i) covered with an inert material having a low surface energy and from which the fibres are easily removed; (ii) covered with a textile from which the fibres are not removed; (iii) an implantable medical device; or (iv) both (i) and (ii) or both (i) and (iii).

10. The method of claim 1, wherein the fibres have a diameter of from 100 nm to 100 μm and form a non-woven 2D or 3D fabric having an area weight of 0.1 to 120 g/$m^2$ on the collector.

11. The method of claim 1, wherein: the spinning solution comprises hyaluronan 3-(2-furanyl) acryloyl ester, or a mixture of hyaluronic acid or a water-soluble salt thereof and hyaluronan 3-(2-furanyl) acryloyl ester having a total concentration of from 1 to 5% by weight of the spinning solution, where the proportion of hyaluronan 3-(2-furanyl) acryloyl ester in the mixture of hyaluronic acid is at least 0.1%, and where the hyaluronan 3-(2-furanyl) acryloyl ester has a degree of substitution of from 0.1 to 20%; wherein the fibres are deposited on the collector in the form of a non-woven fabric; and wherein the method further comprises subsequently crosslinking together the deposited fibres by exposure to radiation with a of from 280 to 750 nm for a period of from 2 to 60 minutes.

12. The method of claim 1, wherein the spinning solution comprises: (i) an auxiliary polymer selected from carboxymethyl cellulose and oxycellulose;

(ii) a pharmaceutically and/or cosmetically acceptable low molecular weight substance selected from antibacterial agents, antivirals, antifungals, algesic or anesthetic drugs, vitamins, plant extracts, surfactants, peptides, dyes, and combinations thereof; or (iii) both (i) and (ii).

13. The method of claim 1, wherein the weight average molecular weight of hyaluronic acid and/or the water-soluble metal or non-metal salt thereof and/or the hyaluronic acid derivative is from 90 kDa to 2.5 MDa.

* * * * *